(12) United States Patent
Radwin et al.

(10) Patent No.: US 10,842,941 B2
(45) Date of Patent: Nov. 24, 2020

(54) SYRINGE ATTACHMENT DEVICE AND METHODS

(71) Applicant: WISCONSIN ALUMNI RESEARCH FOUNDATION, Madison, WI (US)

(72) Inventors: Robert Radwin, Waunakee, WI (US); Joseph Ulbrich, Winneconne, WI (US); Thomas Yen, Fitchburg, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 153 days.

(21) Appl. No.: 16/015,553

(22) Filed: Jun. 22, 2018

(65) Prior Publication Data

US 2018/0369487 A1    Dec. 27, 2018

Related U.S. Application Data

(60) Provisional application No. 62/523,569, filed on Jun. 22, 2017.

(51) Int. Cl.
*A61M 5/14* (2006.01)
*A61J 1/20* (2006.01)
(Continued)

(52) U.S. Cl.
CPC ............ *A61M 5/3137* (2013.01); *A61J 1/201* (2015.05); *A61J 1/2048* (2015.05); *A61J 1/2055* (2015.05);
(Continued)

(58) Field of Classification Search
CPC .............. A61M 5/1458; A61M 5/3137; A61M 5/3138; A61M 5/31526;
(Continued)

(56) References Cited

U.S. PATENT DOCUMENTS 1,718,596 A * 6/1929 Smith .................... A61M 5/24
                                                    604/223
2,722,931 A * 11/1955 May ....................... A61M 5/30
                                                    604/68
(Continued)

FOREIGN PATENT DOCUMENTS

EP          1110569 A2 *  6/2001  .......... A61M 5/1456
WO   WO-2014022750 A1 *  2/2014  .......... A61M 1/0064

OTHER PUBLICATIONS

Innomed Orthopedic Instruments. General Orthopedic Instruments—White Aspiration Handle. Retrieved on Mar. 6, 2019 from http://www.innomed.net/general_orthopedic_htm#WhiteAspirationHandleGen.
(Continued)

*Primary Examiner* — Adam D Rogers
(74) *Attorney, Agent, or Firm* — Seager, Tufte & Wickhem LLP

(57) ABSTRACT

A syringe adapter having a syringe holder and an actuator are disclosed. The syringe holder may include a fixed portion that may receive a barrel of a syringe and an adjustable portion adjustably positioned relative to the fixed portion, where the adjustable portion may receive a plunger of the syringe. To facilitate aspirating fluid to and/or dispensing fluid from the syringe, the actuator may be selectively actuated with one or more digits or a palm of a user's hand to adjust a position of the adjustable portion. The selective actuation of the actuator may be performed with one or more digits of the user while two or more other digits are engaging a portion of the adapter adjacent a dispensing end of the syringe. The adapter may include a gear system translating movement of the actuator to movement of the adjustable portion of the syringe holder.

14 Claims, 25 Drawing Sheets

(51) Int. Cl.
| | |
|---|---|
| *F16H 19/02* | (2006.01) |
| *B05C 17/01* | (2006.01) |
| *A61M 5/31* | (2006.01) |
| *F16H 19/04* | (2006.01) |
| *A61M 5/145* | (2006.01) |
| *A61J 1/22* | (2006.01) |
| *A61M 5/315* | (2006.01) |

(52) U.S. Cl.
CPC ........... *A61J 1/2065* (2015.05); *A61J 1/2096* (2013.01); *A61J 1/22* (2013.01); *A61M 5/1458* (2013.01); *B05C 17/01* (2013.01); *F16H 19/04* (2013.01); *A61J 2200/76* (2013.01); *A61M 2005/3139* (2013.01); *A61M 2005/3152* (2013.01); *A61M 2205/3389* (2013.01); *A61M 2205/581* (2013.01); *A61M 2205/582* (2013.01); *A61M 2205/583* (2013.01)

(58) Field of Classification Search
CPC .. A61M 2005/3139; A61M 2005/3152; A61M 2205/3389; A61M 2205/581; A61M 2205/582; A61M 2205/583; A61J 1/18; A61J 1/201; A61J 1/2048; A61J 1/2055; A61J 1/2065; A61J 1/2096; A61J 1/22; A61J 2200/76; B05C 1/01; B05C 17/0123; B05C 17/01; F16H 1/14; F16H 19/04; F16H 31/001
See application file for complete search history.

(56) References Cited

U.S. PATENT DOCUMENTS

| | | | | |
|---|---|---|---|---|
| 2,725,877 | A * | 12/1955 | Reiter | A61M 5/20 604/135 |
| 2,892,457 | A | 6/1959 | Sturtz | |
| 3,811,442 | A * | 5/1974 | Maroth | A61M 5/20 604/188 |
| 4,231,368 | A * | 11/1980 | Becker | A61M 5/20 604/117 |
| 4,594,073 | A | 6/1986 | Stine | |
| 4,959,056 | A * | 9/1990 | Dombrowski | A61M 5/1782 604/186 |
| 5,115,816 | A | 5/1992 | Lee | |
| 5,135,511 | A | 8/1992 | Houghton et al. | |
| 5,176,646 | A * | 1/1993 | Kuroda | A61M 5/1456 128/DIG. 1 |
| 5,322,511 | A * | 6/1994 | Armbruster | A61M 5/20 604/155 |
| 5,469,860 | A | 11/1995 | De Santis | |
| 5,672,155 | A * | 9/1997 | Riley | A61M 5/20 604/131 |
| 5,743,431 | A | 4/1998 | Brattesani | |
| 5,807,340 | A | 9/1998 | Pokras | |
| 6,003,736 | A * | 12/1999 | Ljunggren | A61M 5/14244 222/309 |
| 7,678,084 | B2 * | 3/2010 | Judson | A61M 5/24 604/110 |
| 8,133,208 | B2 * | 3/2012 | Hetherington | A61M 5/3158 604/207 |
| 8,298,171 | B2 * | 10/2012 | Ishikawa | A61M 5/20 604/65 |
| 8,672,900 | B2 | 3/2014 | Fojtik | |
| 9,114,216 | B2 * | 8/2015 | Sutkin | A61M 5/31526 |
| 9,707,354 | B2 * | 7/2017 | Madsen | A61M 5/31575 |
| 9,724,479 | B2 * | 8/2017 | Sutkin | A61M 5/31581 |
| 9,795,535 | B2 * | 10/2017 | Aguerre | A61J 1/16 |
| 10,099,244 | B2 * | 10/2018 | Pfahnl | A61M 1/0064 |
| 10,213,555 | B1 * | 2/2019 | Carranza | A61M 5/31585 |
| 10,322,227 | B2 * | 6/2019 | Piehl | A61M 5/1408 |
| 10,506,929 | B2 * | 12/2019 | Almoumen | A61M 5/3134 |
| 2005/0215958 | A1 | 9/2005 | Hawthorne | |
| 2005/0261633 | A1 * | 11/2005 | Khalaj | A61M 5/20 604/181 |
| 2006/0069355 | A1 | 3/2006 | Judson et al. | |
| 2006/0217670 | A1 * | 9/2006 | Cecchi | A61M 5/19 604/209 |
| 2014/0018770 | A1 | 1/2014 | Sutkin | |
| 2014/0088553 | A1 | 3/2014 | Hetherington | |
| 2014/0296868 | A1 | 10/2014 | Garrison et al. | |
| 2015/0209821 | A1 | 7/2015 | Pfahnl et al. | |
| 2015/0343147 | A1 | 12/2015 | Franklin et al. | |
| 2017/0326293 | A1 * | 11/2017 | Sims | A61M 5/1456 |
| 2018/0326145 | A1 * | 11/2018 | Jiang | A61M 5/14236 |
| 2019/0336700 | A1 * | 11/2019 | Nober | A61M 5/2033 |
| 2020/0016331 | A1 * | 1/2020 | Lee | A61M 5/14546 |

OTHER PUBLICATIONS

Innomed Orthopedic Instruments. General Orthopedic Instruments—Gray Syringe Assist With Ergonomic Handle. Retrieved on Mar. 6, 2019 from http://www.innomed.net/general_orthopedic.htm#GraySyringeAssistGen.
Radwin, R. G. and J. T. Haney, An Ergonomics Guide to Hand Tools, American Industrial Hygiene Association, 1996.
Muscles of the Forearm [image]. (2013). https://noexcuseshealth.wordpress.com/2013/03/20/forearm-exercise-reverse-wrist-curls/.
Qin, J., Chen, H., and Donnerlein, J. (2013). "Wrist posture affects hand and forearm muscle stress during tapping." Applied Ergonomics (44). doi: 10.1016/j.apergo.2013.03.013.
San Chun, Keum, Ngoc Phung, Kevin Wreoatmodjo, and Alex Eaton. Techniques for Eliminating Extensor Forces on the Thumb during Rat Gavage. Tech. N.p., May 2015. Web. Sep. 15, 2015.
Swanson, Alfred B., Ivan Matev, and G. De Groot. "The Strength of the Hand." ICIB 13.10 (1974): 1-8. Web.
Richards, Robin R., Robert Gordon, and Dorcas Beaton. "Measurement of Wrist, Metacarpophalangeal Joint, and Thumb Extension Strength in a Normal Population." Science Direct. The Journal of Hand Surgery, Mar. 1993. Web. Sep. 15, 2015.
Nimunkar, A. J., San Chun, K., Phung, N., Wreksoatmodjo, K., Yen, T. Y., and Radwin, R. G. (2017). "Reducing thumb extensor risk in laboratory rat gavage." Applied ergonomics, 58, 151-155.
J.M. Harrington, J.T. Carter, L. Birrell, and D. Gompertz, Surveillance case definitions for work related upper limb pain syndromes Occup. Environ. Med., 55 (4) (1998), pp. 264-271.
Victoria MacDonald & Peter J. Keir. "Assessment of Musculoskeletal Disorder Risk with Hand and Syringe use in Chemotherapy Nurses and Pharmacy Assistants." IISE Transaction on Occupational Ergonomics and Human Factors. (2018). ISSN: 2472-5838 (Print) 2472-5846 (Online) Journal homepage: http://www.tandfonline.com/loi/uehf21.

* cited by examiner

SYRINGE ATTACHMENT DEVICE AND METHODS

CROSS REFERENCE TO RELATED APPLICATIONS

This application claims the benefit of U.S. Provisional Patent Application Ser. No. 62/523,569, filed Jun. 22, 2017, the disclosure of which is incorporated herein by reference.

TECHNICAL FIELD

The disclosure pertains to syringe attachment devices, and methods for manufacturing and/or using syringe attachment devices. More particularly, the present disclosure pertains to syringe adapters and methods that facilitate aspirating fluid to and/or dispensing fluid from a syringe.

BACKGROUND

A wide variety of attachment devices for use with syringes have been developed. Such attachment devices for use with syringes may be used to fill a syringe with fluid and/or dispense fluid from a syringe. These attachment devices are manufactured by any one of a variety of different manufacturing methods and may be used according to any one of a variety of methods. Of the known attachment devices for use with syringes and associated methods, each has certain advantages and disadvantages.

SUMMARY

The disclosure is directed to several alternative designs, materials, and methods of manufacturing syringe adapter structures and assemblies. Although it is noted that conventional attachment devices for use with syringes are known, there exists a need for improvement on those devices.

Accordingly, one illustrative instance of the disclosure may include a one-handed syringe adapter. The syringe adapter may include a syringe holder and an actuator. The syringe holder may have a fixed portion and an adjustable portion adjustably positioned relative to the fixed portion. The fixed portion may be configured to receive a barrel of a syringe and the adjustable portion may be configured to receive a plunger of the syringe. In some cases, the actuator may be selectively actuated with a palmar flexion movement of one or more digits of a user's hand to adjust a position of the adjustable portion of the syringe holder relative to the fixed portion of the syringe holder while two or more other digits of the user's hand engage the syringe adapter.

Another illustrative instance of the disclosure may include an adapter comprising a body, a gripping portion, and an actuator. The body may be configured to receive a syringe and may include a fixed first portion, an adjustable second portion, a first end portion, and a second end portion. The adjustable second portion may be adjustable with respect to the fixed first portion in directions toward and/or from the first end portion. The second end portion may be adjacent an end of the body opposite an end of the body adjacent the first end portion. In some cases, the gripping portion may be adjacent the second end portion of the body and the actuator may be offset toward the first end portion of the body relative to the gripping portion and movable relative to the gripping portion. Movement of the actuator may generate movement of the adjustable second portion of the body to adjust a position of the adjustable second portion relative to the fixed first portion.

Another illustrative instance of the disclosure may include a handheld syringe adapter having a body, an actuator, and a gear system. The body may be configured to receive a syringe and may include a fixed first portion, an adjustable second portion, a first end portion, and a second end portion. The adjustable second portion may be adjustable with respect to the fixed first portion toward and/or from the first end portion adjacent a first end of the body. The second end portion may be adjacent a second end of the body that is opposite the first end. The actuator may be adjustable about a first axis and the gear system may include one or more gear components rotatable about a second axis that may be non-parallel with the first axis. Actuation of the actuator about the first axis may cause rotation of the one or more gears about the second axis and adjust a position of the adjustable second portion.

The above summary of some example embodiments is not intended to describe each disclosed embodiment or every implementation of the disclosure.

DESCRIPTION OF THE DRAWINGS

The disclosure may be more completely understood in consideration of the following detailed description of various embodiments in connection with the accompanying drawings, in which.

Figure 1:
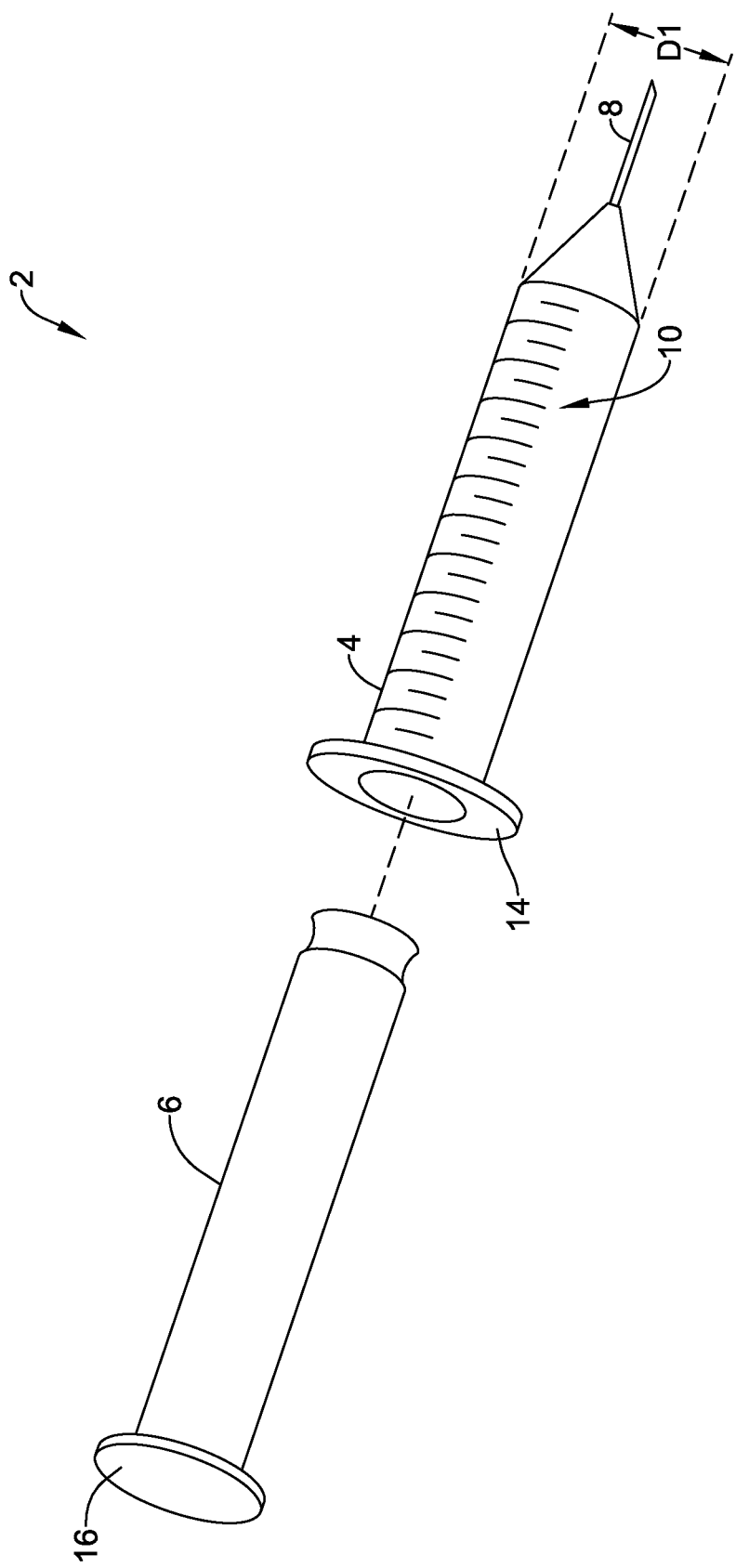
FIG. 1 is an exploded perspective view of a syringe having a syringe barrel and a plunger.

While the disclosure is amenable to various modifications and alternative forms, specifics thereof have been shown by way of example in the drawings and will be described in detail. It should be understood, however, that the intention is not to limit aspects of the claimed disclosure to the particular embodiments described. On the contrary, the intention is to cover all modifications, equivalents, and alternatives falling within the spirit and scope of the claimed disclosure.

DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the claimed disclosure. The illustrative embodiments depicted are intended only as exemplary. Selected features of any illustrative embodiment may be incorporated into an additional embodiment unless clearly stated to the contrary.

Figure 2:
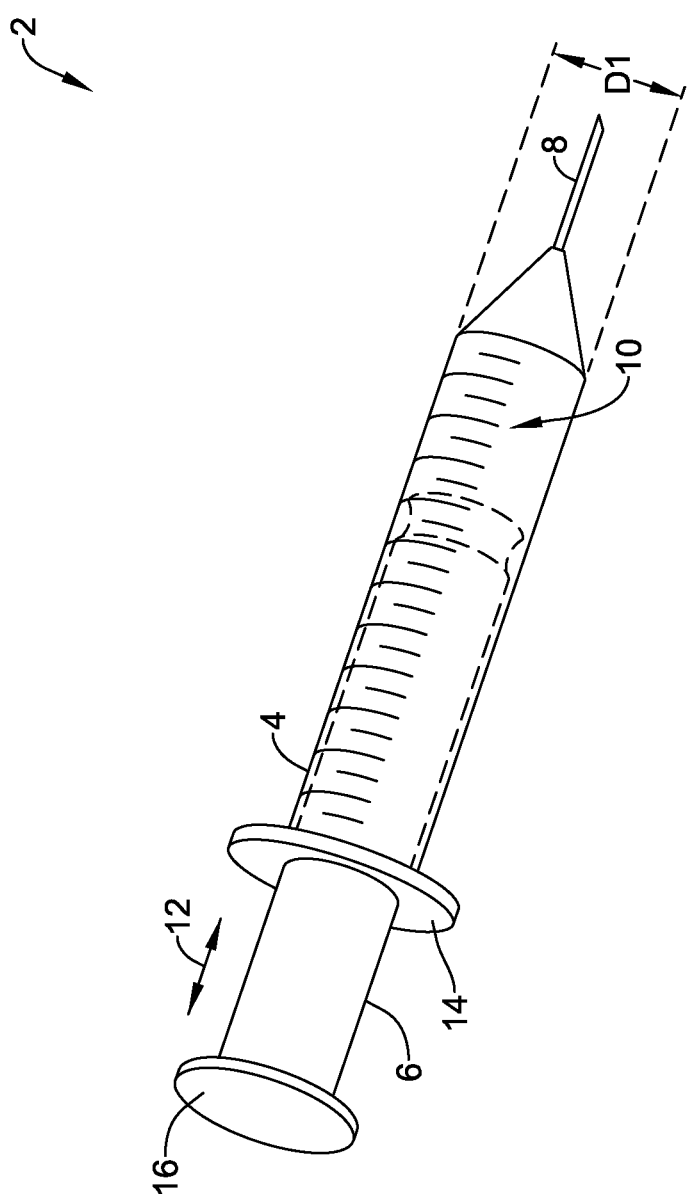
FIG. 2 is a perspective view of the syringe of FIG. 1 with the plunger inserted into the syringe barrel.

Referring to the Figures, FIG. 1 and FIG. 2 depict a syringe 2. FIG. 1 depicts the syringe 2 in an exploded view and FIG. 2 depicts the syringe 2 in an assembled view.

The syringe 2 may include a barrel 4 and a plunger 6. The barrel 4 may include a reservoir for holding fluid aspirated into the barrel 4 and/or to be dispensed from the barrel 4. In some cases, the barrel 4 may include indicia 10 providing measurement labels visible from exterior the syringe and/or other information. The indicia 10, when in measurement label form, may be in any unit of measurement useful for measuring volume (e.g., of a fluid) and may be provided in any desired increment. Further, the syringe 2 may include a needle 8, as shown in FIGS. 1 and 2, with a lumen there through for dispensing fluid from the barrel 4 and/or aspirating fluid into the barrel 4 and a sharpened end to facilitate inserting the needle 8 into an animal (e.g., a human or other animal), vial, and/or other object, but this is not required. Alternatively, the syringe 2 may include a nozzle or cannula with a lumen and a blunt end, or one or more other configurations. Although FIGS. 1 and 2 depict the syringe 2 having a tapered transition from a diameter having a distance D1 (e.g., of the barrel 4) toward the needle 8, other transitions between the barrel 4 and the needle 8 may be utilized.

As depicted in FIG. 2, the plunger 6 may be positioned within the barrel 4 of the syringe 2 (note: the portion of the plunger 6 inserted into the barrel 4 is shown in broken lines). As indicated by the directional arrows 12, the plunger 6 may be at least partially inserted into and/or withdrawn from the barrel 4 of the syringe 2. Inserting the plunger 6 at least partially into the barrel 4 of the syringe 2 may result in dispensing fluid from the barrel 4 through the needle 8 or other portion of the syringe 2 having a lumen open to an exterior of the barrel 4. Withdrawing the plunger 6 at least partially from the barrel 4 may result in aspirating fluid into the barrel 4 through the needle 8 or other portion of the syringe 2 having a lumen open to an exterior of the barrel 4.

The barrel 4 of the syringe 2 may include a flange 14, as shown for example in FIGS. 1 and 2. The flange 14 may provide an interface to facilitate a user and/or equipment holding or grasping the barrel 4 during use of the syringe 2. Although the flange 14 is shown in FIGS. 1 and 2 at an end of the barrel 4 opposite an end of the barrel 4 from which the needle 8 extends, one or more flanges 14 may be located at one or more locations between ends of the barrel 4.

The plunger 6 of the syringe 2 may include a flange 16, as shown for example in FIGS. 1 and 2. The flange 16 may provide an interface to facilitate a user and/or equipment holding or grasping the plunger 6 during use of the syringe 2. Although the flange 16 is shown in FIGS. 1 and 2 at an end of the plunger 6, one or more flanges 16 may be located at one or more locations along a length of the plunger 6.

Figure 3:
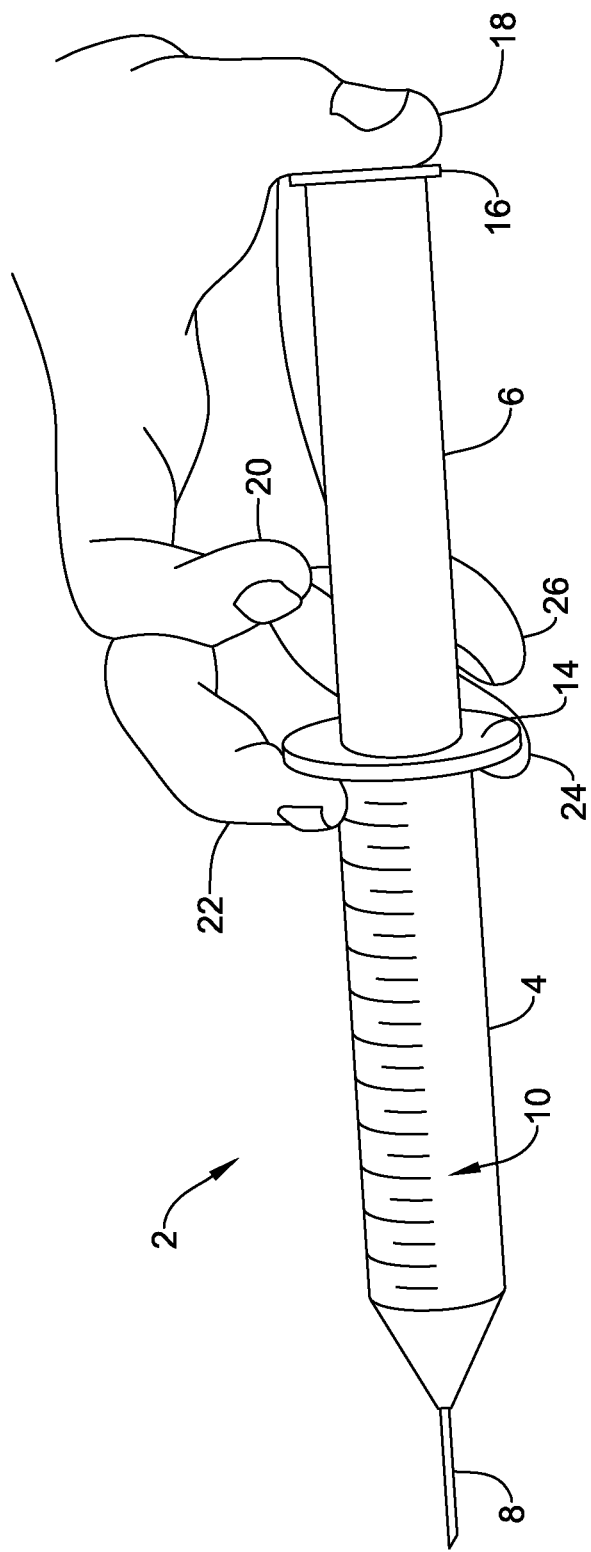
FIG. 3 is a side view of a user holding the syringe of FIG. 1 in a dispensing position.

FIG. 3 depicts one manner in which a user may hold a syringe 2 for dispensing a fluid with a single hand without assistance from an attachment device that facilitates advancing the plunger 6 into the barrel 4 of the syringe. In this example, a third digit 22 and a fourth digit 24 of a user are placed on the barrel 4 (e.g., on the flange 14) and a first digit 18 of the user is placed on the flange 16 of the plunger 6. To advance the plunger 6 within the barrel 4 of the syringe 2 and dispense fluid from the barrel 4, the user may squeeze or otherwise apply a force to the flange 14 of the barrel 4 and/or the flange 16 of the plunger 6. Although FIG. 3 depicts an example configuration for holding a syringe 2 for the purpose of dispensing fluid, other configurations may be used. Further, as used herein and as commonly understood in the art, a user's first digit 18 is commonly known as a thumb, a user's second digit 20 is commonly known as an index finger, a user's third digit 22 is commonly known as a middle finger, a user's fourth digit 24 is commonly known as a ring finger, and a user's fifth digit 26 is commonly known as a pinky.

The ability to squeeze and/or apply a dispensing force to a syringe 2 may be difficult, particularly when the syringe 2 is full of fluid and/or at other times. One factor contributing to this difficulty may be an increasing distance between the first digit 18 of a user engaging the flange 16 of the plunger and other digits of the user engaging the barrel 4. As this distance approaches a maximum reach of a hand, the squeeze force that a user may be capable of applying decreases. Further, when a user's hand is small, the user's hand may not be large enough to reach between the flange 16 of the plunger 6 and the flange 14 of the barrel 4 to initiate dispensing fluid from the syringe 2 with one hand. Additionally, a user may be at risk of injury by dispensing fluid in the manner shown in FIG. 3, as strain may be imposed on finger tendons and associated anatomical structures while engaging the plunger.

Figure 4:
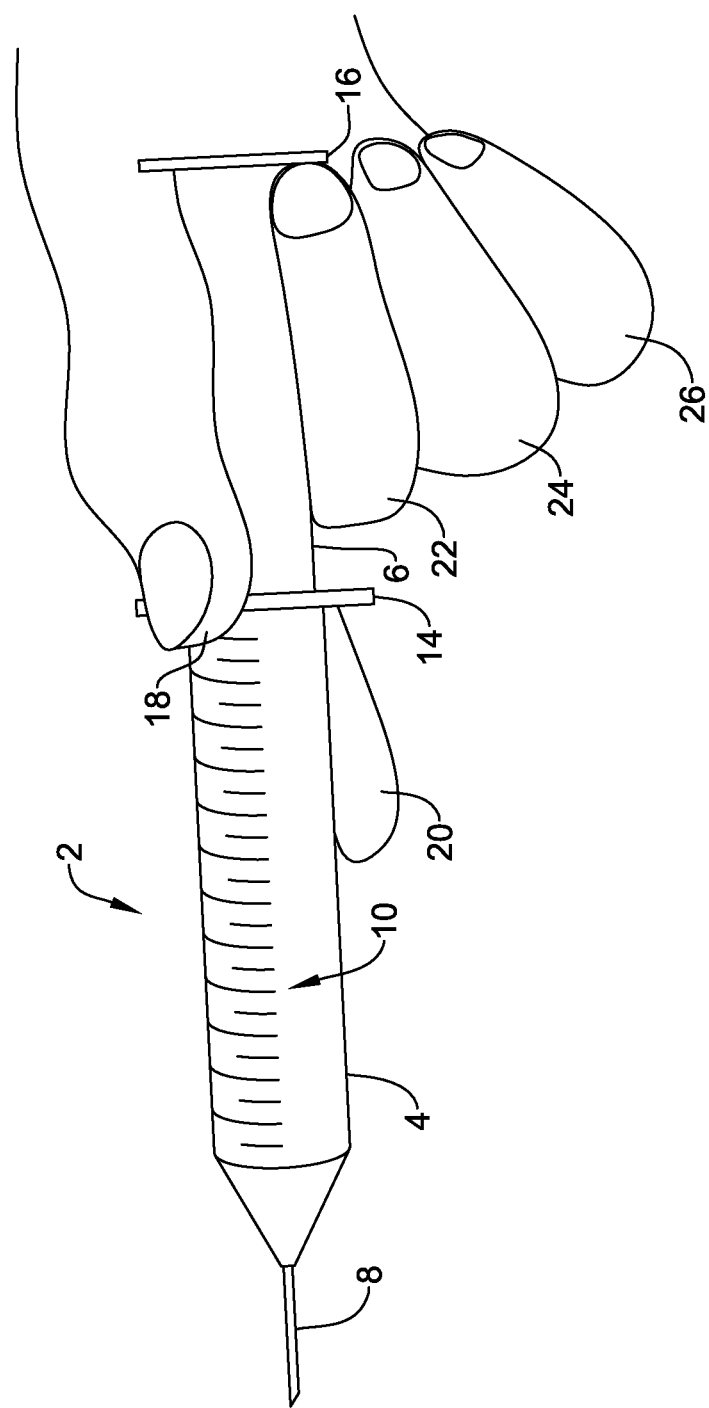
FIG. 4 is a side view of a user holding the syringe of FIG. 1 in an aspirating position.

FIG. 4 depicts one manner in which a user may hold a syringe 2 for aspirating a fluid with a single hand without assistance from an attachment device that facilitates withdrawing the plunger 6 from the barrel 4 of the syringe 2. In this example, a first digit 18 of a user and a second digit 20 of the user may be placed on the barrel 4 and/or the flange 14 to grip the syringe 2. Alternatively, the user may place one or more other digits on the barrel 4 and/or the flange 14 to grip the syringe 2. To draw back on the plunger 6 while gripping the barrel 4, a third digit 22 (as shown in FIG. 4) or a fourth digit 24 of the user engages the flange 16 of the plunger 6 and the user flexes, laterally bends, and/or abducts the digit (e.g., with a combined over flexion and extension of the digit) to apply a force on the flange 16 causing the plunger 6 to withdraw from the barrel 4 and aspirate fluid into the syringe 2. Gripping or pinching the barrel 4 with two digits may allow the user to stabilize the syringe 2 while applying a force to the flange 16 of the plunger 6 during aspiration.

Users may hold a syringe 2 in one or more manners other than what is depicted in FIG. 4 to aspirate a fluid into the syringe 2 with a single hand. In one example hold, the first digit of a user's hand may engage the flange 16 of the plunger 6 while the barrel 4 of the syringe 2 is held with two or more other digits (e.g., the second and third digits and/or other digits) of the user's hand. Other one-handed aspiration techniques are known.

The ability to fully extend the plunger 6 relative to the barrel 4 may be difficult with one hand, particularly when a distance between the flange 14 of the barrel 4 and the flange 16 of the plunger 6 increases. As this distance reaches a maximum reach of a user's hand, the pushing force a user may be capable of applying apply decreases. Moreover, when the distance is greater than a distance the user's third digit 22 or fourth digit 24 may flex, bend, and/or abduct relative to the first digit 18 and the second digit 20 gripping the barrel 4, the user may not be able to fully extend the plunger 6 to completely fill the syringe 2 using only a single hand.

Further, a user may be at risk of discomfort, strain, and/or an injury by using only one digit to draw back the plunger 6 in the manner shown in FIG. 4 due to over or hyper flexion of the digit drawing back the plunger, which may result in tendons and other anatomical structures in and/or around the hand extending to limits of their ranges of motion and causing strain on those tendons and anatomical structures. For example, when making the palmar flexion motion depicted in FIG. 4 with one or both of the third digit 22 and the fourth digit 24, the associated extensor digitorum tendon(s) may be over extended and both of the associated superficial digital flexor muscle and deep digital flexor muscle (e.g., also known as the flexor digitorum profundis) may be over flexed. Other examples are contemplated.

In addition to the difficulties and/or risks of discomfort, strain, and/or injury when performing the dispensing and/or aspiration techniques discussed above, a user may experience difficulties and/or may be at risk of discomfort, strain, and/or injury as a result of preparing a syringe for dispensing and/or using a syringe into which fluid has been aspirated. For example, preparing a syringe for dispensing may include aspirating fluid into the syringe and similar difficulties and/or discomforts, strains, and/or injuries to those discussed above with respect to the aspiration techniques depicted in FIG. 4, and/or other aspiration techniques, may be realized. Similarly, using a syringe into which fluid has been aspirated may include dispensing fluid from the syringe and similar difficulties and/or discomforts, strains, and/or injuries to those discussed above with respect to the dispensing techniques depicted in FIG. 3, and/or other dispensing techniques, may be realized.

One handed syringe dispensing and aspirating are performed in a variety of industries including, but not limited to, animal testing and/or medical applications. For example, the one-handed fluid dispensing procedure discussed above with respect to FIG. 3 may be performed by a technician in an animal testing laboratory many times per day to inject fluid into an animal. As a result, such a technician places a significant amount of stress on anatomy surrounding the first digit 18, including but not limited to on their hand, wrist, and forearm muscles, tendons, ligaments, sheaths, joints, and/or other anatomy. In another example, the one-handed fluid aspirating procedure discussed above with respect to FIG. 4 may be performed by a single animal testing technician many times per day (e.g., 120 times or more per day). As a result, such technicians place a significant amount of stress and strain on their hand, wrist, and forearm muscles, tendons, ligaments, sheaths, and joints, and particularly the user's third digit 22 extensor digitorum tendon, which interacts with a user's extended second digit 20. In yet another example, the one-handed fluid aspirating procedure discussed above with respect to FIG. 4 may be performed by a medical professional to perform central line placements. When performing central line placements, the medical professional must find a desired vein, while maintaining a negative pressure within the barrel of the syringe when pushing the syringe deeper into a patient. Such a procedure may result in medical professionals placing a tremendous amount of stress for a prolonged period of time (e.g., the procedure may take between ten (10) and forty-five (45) minutes or longer) on their hand, wrist, and forearm muscles, tendons, ligaments, sheaths, and joints, and particularly the user's third digit 22 extensor digitorum tendon, which interacts with the user's extended second digit 20, to maintain the negative pressure during the procedure and ensure it is known when the syringe needle enters a vein. In a further example, similar forces may be applied to medical professionals performing thoracentesis, which may require a medical professional to apply and maintain a negative pressure to a syringe while advancing the syringe into a patient to ensure a pressure in the patient's chest cavity does not change as a pressure differential between the lungs and the diaphragm may inadvertently collapse a lung. These are just some example procedures using one-handed dispensing and/or aspirating techniques and others are contemplated.

FIGS. 5-25 depict various features of illustrative syringe attachment devices or adapters. FIGS. 5-13 depict various features of syringe attachment devices or adapters in a context of an illustrative syringe attachment device or adapter 100. FIGS. 14-21 depict various features of syringe attachment devices or adapters in a context of an illustrative syringe attachment device or adapter 300. FIGS. 22-25 depict various features of a syringe attachment devices or adapters in a context of an illustrative syringe attachment device or adapter 500. Although various features of syringe attachment devices or adapters are depicted and described in a context of the syringe attachment device or adapter 100, the syringe attachment device or adapter 300, and the syringe attachment device or adapter 500, the features described herein may be utilized with and/or form part of one or more other suitable syringe attachment devices or adapters.

The features of the adapters 100, 300, 500 may provide users the ability to perform one-handed syringe procedures more accurately, safely, and comfortably than what can be achieved without use of attachment devices (e.g., using the procedures discussed above with respect to FIGS. 3 and 4). For example, the adapters 100, 300, 500 or other suitable adapters including features described herein may provide a better position for holding the syringe when aspirating fluid into the syringe due to including grip features that may be separated by a distance greater than a distance of a diameter of a syringe (e.g., a distance D1, as depicted in FIG. 1) and may allow for less strain on a user's hand by changing the motion required for adjusting a plunger relative to a barrel of a syringe from a combined over-flexion and extension motion (e.g., flexion of a third digit and a fourth digit down to a wrist of a user) to a flexion motion within a desired range humans are fully capable of comfortably making without loss of force generation. Similar benefits may be achieved by using adapters 100, 300, 500 for dispensing fluid from a syringe. Additionally, the adapters 100, 300, 500, or other suitable adapters including features described herein may provide similar benefits over other types of syringe attachment devices which may not facilitate stabilizing a syringe with two digits and/or a palm of a hand while allowing for a flexing movement to adjust a plunger relative to a barrel of a syringe.

Figure 5:
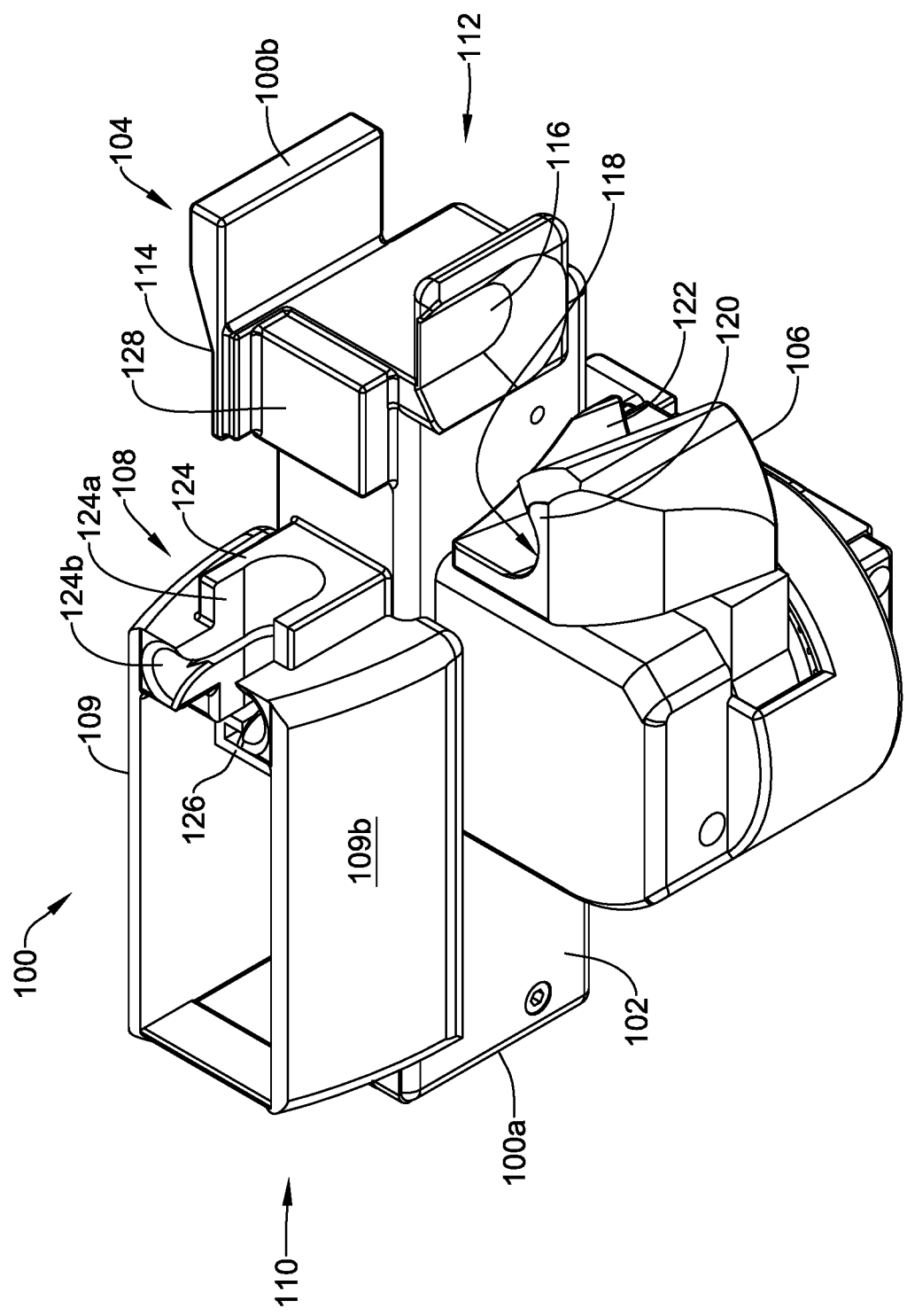
FIG. 5 is a perspective view of an example adapter for use with a syringe.

FIG. 5 is a perspective view of the illustrative adapter 100 configured to be used with a syringe (e.g., a syringe 2 or other syringe). In some cases, the adapter 100 may include a housing 102, a gripping portion 104, an actuator 106, a syringe holder 108, and a support portion 109, among other features or components. One or more of the housing 102, the gripping portion 104, the actuator 106, the syringe holder 108, the support portion 109, and/or other components of the adapter 100 may form a body of the adapter 100. The body of the adapter 100 may have a first end portion 110 adjacent a first end 100a of the adapter 100 and a second end portion 112 adjacent a second end 100b of the adapter 100 opposite the first end 100a.

The housing 102 may at least partially cover one or more components of the adapter 100. In one example, the housing 102 may at least partially cover an actuation system (e.g., an actuation system 150, discussed in greater detail below, or other actuation systems) of the adapter 100. Further, in some cases, the housing 102 may at least partially form one or more other features of the adapter 100 including, but not limited to, the gripping portion 104, the actuator 106, the syringe holder 108, and/or the support portion 109. In some cases, the housing 102 may be omitted and/or entirely formed from other components of the adapter 100.

The gripping portion 104 may be any portion of the adapter configured to allow a user to grip or otherwise engage the adapter 100 with one or more digits. In one example, the gripping portion 104 may be configured to allow a user to apply a pinching force to the gripping portion 104 to steadily hold or grasp the adapter 100. Structurally, in some cases, the gripping portion 104 may be or may include extensions (e.g., flanges or other extensions) of or extending from the housing 102, that may be, or may be formed in, sides of the housing 102 (e.g., opposing sides of the housing 102 or other sides of the housing 102), and/or may include one or more other features of or extending from the body of the adapter 100.

The gripping portion 104 may be located adjacent to the second end portion 112 of the body of adapter 100 and may include one or more grip portions. In one example, the gripping portion 104 may include a first grip portion 114 and a second grip portion 116. Alternatively, the gripping portion 104 may include a single grip portion or more than two grip portions. The first grip portion 114 and the second grip portion 116 may be configured to receive one or more digits of a user. In one example, the first grip portion 114 may be configured to receive an initial digit of a user (e.g., a user's first digit 18 or other digit) and the second grip portion 116 may be configured to receive another digit of the user (e.g., the user's second digit 20 or other digit). When a user is gripping the gripping portion 104 with two digits in the manner of the example, a palm of the hand with which the user is gripping the gripping portion 104 may be facing the body of the adapter 100 and disposed toward the first end portion 110 relative to the portions of the user's digits gripping the gripping portion 104.

In some cases, portions of the gripping portion 104 may include one or more gripping features. For example, the first grip portion 114 and/or the second grip portion 116 may be or may have indents, contours, bumps, lines, smooth surfaces, and/or other gripping features to facilitate receiving one or more digits of a user. Alternatively or in addition, one or more of the grip portions 114, 116 may not have any gripping features.

The actuator 106 may be part of or may be in communication with the actuation system of the adapter 100. Further, the actuation system may comprise a gear system and/or one or more other actuation sub-systems (e.g., pneumatic, hydraulic, pulley, or other suitable actuation sub-system) configured to adjust a portion of the syringe holder 108 (discussed in greater detail below). In some cases, the actuator 106 may be in communication with an actuation sub-system at least partially within the housing 102 and may extend out of the housing 102 to be accessible by a user from exterior of the housing.

The actuator 106 may be or may include a grip portion 118 (e.g., a third grip portion). To facilitate actuation of the actuator 106 with one or more digits of a user and/or for other purposes, the grip portion 118 may have a first support 120 and/or a second support 122. The first support 120 may be configured to engage one or more digits of a user when loading the actuator 106 or actuation system with a laterally outward motion from the housing 102, the gripping portion 104, and/or the syringe holder 108. The second support 122 may be configured to engage one or more digits of a user when actuating the actuator 106 or actuation system with a laterally inward motion toward the housing 102, the gripping portion 104, and/or the syringe holder 108 to drive a portion of the syringe holder 108. Alternatively or in addition, portions of the grip portion 118 may be engaged by one or more digits or other portions of a hand of a user in one or more suitable manners other than during laterally inward or outward motions relative to the housing 102, the gripping portion 104, and/or the syringe holder 108 to drive a portion of the syringe holder 108. Movement of the actuator 106 (e.g., loading and actuating the actuator 106 or the actuation system) will be described in greater detail below.

The grip portion 118 may take on a suitable shape and/or configuration. In some cases, the first support 120 and the second support 122 may form a crescent-like or hook-like shape, as shown for example in FIG. 5, to facilitate engaging a user's digit(s) when adjusting the actuator 106. Alternatively or in addition, the grip portion 118 may be circumferentially closed with an opening for receiving one or more digits of a user (e.g., similar to some scissors handles), the grip portion 118 may have a paddle shape for engaging one or more digits or other portions of a hand of a user, and/or other suitable shape and/or configuration for engaging one or more portions of a user's hand.

As discussed, the grip portion 118 of the actuator 106 may be configured to receive one or more digits of a user. The grip portion 118 of the actuator 106 may be configured to receive a single digit of a user (e.g., a third digit 22, a fourth digit 24, or other digit of a user), as shown in FIG. 5. Alternatively, the actuator 106 may be configured to receive two or more digits of a user in a side-by-side or spaced relationship. To facilitate additional digits of a user, the actuation system of the adapter 100 may be adjusted toward the first end 100a of the adapter 100 and/or the actuator 106 may be elongated. In one example, the first support 120 and/or the second support 122 of the grip portion 118 may be elongated (e.g., paddle shaped) to facilitate receiving two or more digits of a user. Although the adapter 100 may be configured to easily allow a user to aspirate fluid into a syringe and/or dispense fluid from the syringe by engaging the actuator 106 with a single digit, having an actuator 106 that may accept a plurality of digits may further reduce stress on a user's hand, wrist, and/or forearm areas.

The grip portions 114, 116, 118 may be configured in a suitable manner. In some cases, the grip portions 114, 116, 118 may be sides of the gripping portion 104 or the actuator 106, respectively. Alternatively or in addition, the grip portions 114, 116, 118 may be or may include one or more surfaces, one or more flanges, one or more supports, and/or other structure configured to facilitate maintaining a grip when engaging the gripping portion 104 and/or the actuator 106.

Although the grip portions 114, 116, 118 and/or other grip portions may be depicted in the Figures as having a fixed configuration, the grip portions 114, 116, 118 may be adjustable to facilitate use of the adapter 100 with different sizes of hands. In one case, one or more features of the grip portions 114, 116, 118 may be adjustable relative to other features of the grip portions 114, 116, 118 and/or the housing 102 to facilitate configuring the grip portions 114, 116, 118 such that a hand of a user may comfortably engage the adapter 100. Alternatively or in addition, one or more features of the grip portions 114, 116, 118 may be interchangeable with other suitable configurations of features for the grip portions 114, 116, 118 (e.g., via adhesive, slide fits, friction fits, snap fits, and/or other suitable connections) to provide grip portions for the adapter 100 that facilitate a hand of a user comfortably engaging the adapter 100.

The syringe holder 108 may be at least partially formed from and/or may extend from the housing 102 at a location forming and/or between the first end 100a and the second end 100b of the adapter 100. The syringe holder 108 may be located along a length of the adapter 100 such that when a syringe is received within the syringe holder 108, an object engaging end or dispensing end of the syringe extends distally of the second end 100b of the adapter 100 (e.g., see FIGS. 11-13, discussed below).

The syringe holder 108 may include, among other components, a fixed portion 124 (e.g., a fixed first portion) and an adjustable portion 126 (e.g., an adjustable second portion). The fixed portion 124 of the syringe holder 108 may be configured to receive a barrel (e.g., the barrel 4 or other barrel of a syringe), a barrel flange (e.g., the barrel flange 14 or other barrel flange of a syringe), and/or one or more other portions of a barrel of a syringe. As shown in FIG. 5, for example, the fixed portion 124 may include a first portion 124a configured to receive the barrel of a syringe and a second portion 124b configured to receive a barrel flange, but this is not required. The adjustable portion 126 of the syringe holder 108 may be configured to receive a plunger flange (e.g., the plunger flange 16 or other plunger flange of a syringe), a plunger stem, and/or other portion of a plunger of a syringe. The components of the syringe holder 108 may be adjustable and/or interchangeable with other components or otherwise configured to receive different sizes of syringes.

The fixed portion 124 and the adjustable portion 126 may be configured to secure the syringe in the syringe holder 108 via a friction fit, a snap fit, and/or through other suitable securing mechanisms. In some cases, the fixed portion 124 and/or the adjustable portion 126 may include adjustable components that are adjustable to facilitate different sizes of syringes. In one example, one or more of the fixed portion 124 and the adjustable portion 126 may include one or more inserts or sub-adapters for accommodating different sizes of plunger flanges, barrel flanges, or other components of a syringe. Such inserts or sub-adapters may be releasably connected to and/or positioned within the syringe holder 108.

Although not depicted in FIGS. 5-9, the syringe holder 108 or other suitable portion of the adapter 100 may include a locking mechanism configured to facilitate securing a received syringe within the adapter 100. In some cases, the locking mechanism may be adjustable (e.g., automatically and/or manually adjustable) to releasably secure a received syringe within the adapter 100.

The fixed portion 124 of the syringe holder 108 may be formed from one or more components and may be rigidly fixed or fixedly adjustable relative to the housing 102 and/or the gripping portion 104. In one example, a distance between the fixed portion 124 and the gripping portion 104 may be adjustable to facilitate receiving different lengths of syringes, but this is not required and the fixed portion 124 may be rigidly fixed with respect to the housing 102, the gripping portion 104, or one or more other components of the adapter 100.

The adjustable portion 126 of the syringe holder 108 may be formed from one or more components and may be in communication with the actuation system of the adapter and may be axially and/or longitudinally adjustable relative to the fixed portion 124 of the syringe holder 108. As the adjustable portion 126 may be configured to receive and/or engage a plunger of a syringe, adjusting the adjustable portion of the syringe holder 108 may result in aspirating fluid into the syringe and/or dispensing fluid from the syringe.

As used herein, a first element fixed relative to a second element of the adapter (e.g., the adapter 100, the adapter 300, the adapter 500, or other suitable adapter) may be rigidly fixed relative to the second element or adjustably fixed relative to the second element. A rigidly fixed element may be an element that cannot be adjusted with respect to at least one other element without damaging or changing the intended configuration of the adapter and an adjustably fixed element may be adjustably positioned with respect to at least one other element, but is configured to be fixed relative to the at least one other element while using the adapter to aspirate and/or dispense material from a syringe. An example of an adjustably fixed element may be a gripping portion of an adapter that may be adjusted relative to the syringe holder to accommodate different sizes of users' hands and/or different sizes of syringes, but is placed in a fixed relationship with respect to the syringe holder while aspirating and/or dispensing material from the syringe. Other examples are contemplated.

The adapter 100 may include a syringe support 128, but this is not required. The syringe support 128 may be formed from one or more components and may be part of and/or separate from the syringe holder 108. When part of the syringe holder 108, the syringe support 128 may be separate from or may be part of (e.g., may be an extension of) the fixed portion 124. The syringe support 128 may be configured to support a barrel of a syringe received in the syringe holder 108 and may be located distally of, and/or toward the second end 100*b* of the adapter 100 relative to, the fixed portion 124 of the syringe holder 108. The syringe support 128 may be a platform (e.g., as depicted in the Figures) and/or may be contoured to receive a barrel of a syringe and/or secure the syringe to the adapter 100.

The support portion 109 may provide one or more surfaces for engaging a user's hand (e.g., a palm of the user's hand) while the user is grasping the adapter 100 (e.g., while the user is gripping the first grip portion 114 and/or the second grip portion 116). In some cases, the support portion 109 may cover and/or extend over at least a portion of the syringe holder 108 and/or a syringe received in the syringe holder 108, but this is not required. As such, the support portion 109 may be at least partially configured to prevent a user's hand (e.g., palm or other portion of the user's hand) from engaging a syringe received in the adapter 100 while grasping the adapter 100. As shown in the example of FIG. 5, the support portion 109 may extend from a location adjacent the fixed portion 124 of the syringe holder 108 to a location toward the first end 100*a* of the adapter 100 near where the adjustable portion 126 of the syringe holder 108 is configured to extend. The support portion 109 may be formed from a single part or may include two or more parts adjacent to one another and/or spaced from one another.

Figure 6:
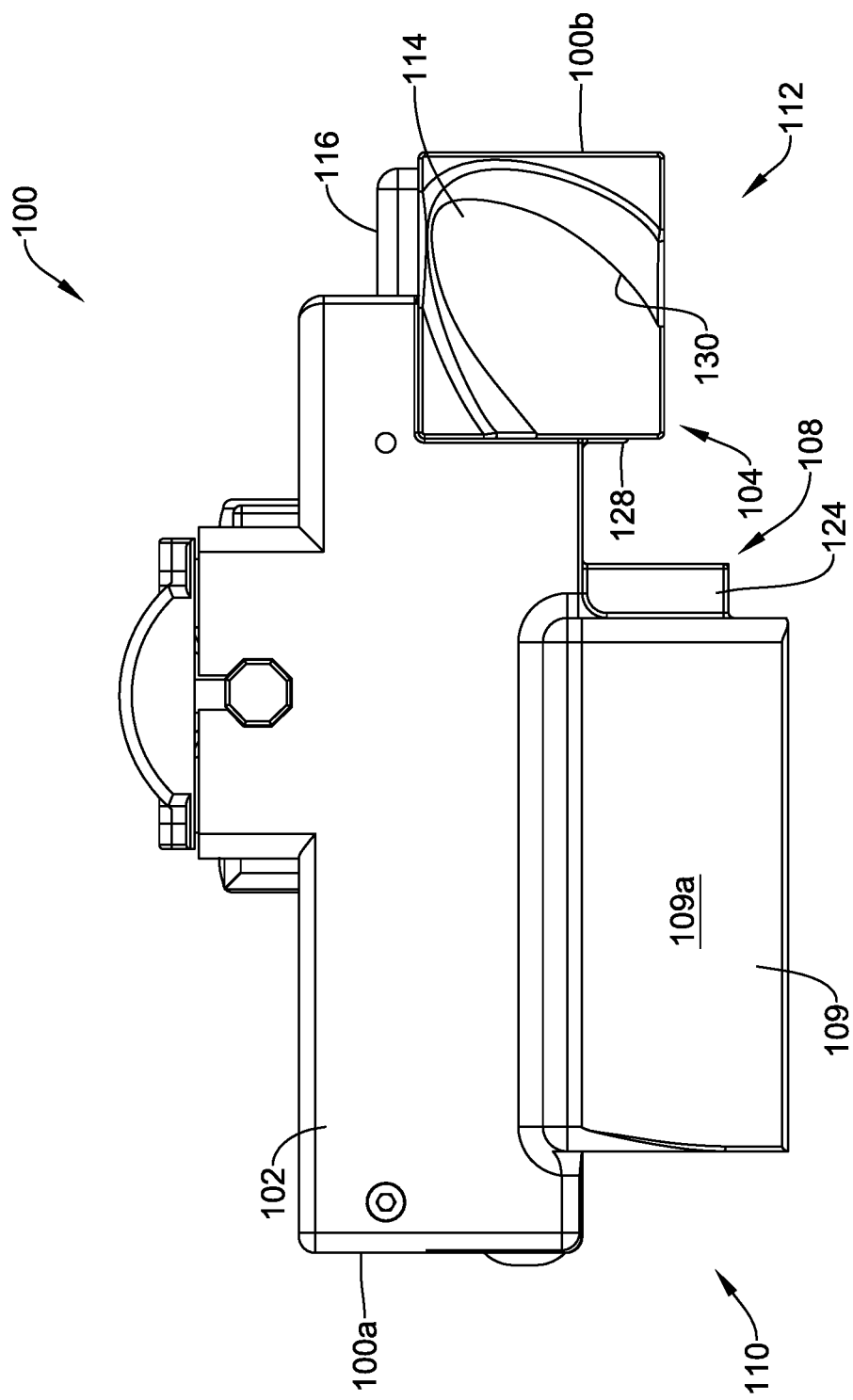
FIG. 6 is a first side view of the example adapter of FIG. 5.

In some cases, the support portion 109 may have at least two surfaces configured to engage a user's hand while the user is grasping the adapter 100. In the example shown in the figures, the support portion 109 may have a first surface or wall 109*a* (e.g., as shown in FIG. 6) and a second surface or wall 109*b* (e.g., as shown in FIGS. 5, 7, and 11-13). The first wall 109*a* and the second wall 109*b* may be positioned such that a palm of a user's hand that is grasping the adapter 100 with two digits engaging the gripping portion 104 may be supported by one or both of the first wall 109*a* and the second wall 109*b*. Additionally, the first wall 109*a* and the second wall 109*b* may be contoured (e.g., rounded or otherwise contoured) to facilitate receiving a palm or other portion of a user's hand. Further, the support portion 109 may include one or more other walls, surfaces, and/or structures for providing support to a user's hand grasping the adapter and/or for one or more other purposes in addition to or as an alternative to the first wall 109*a* and/or the second wall 109*b*.

FIG. 6 is a top side view of the adapter 100. As can be seen in FIG. 6, the first grip portion 114 and the second grip portion 116 of the gripping portion 104 may be located at or adjacent the second end 100*b* of the adapter 100. Further, as depicted in FIG. 6, the syringe support 128 (which is partially hidden and/or disposed behind the gripping portion 104) and the fixed portion 124 of the syringe holder 108 may be spaced from and/or located toward the first end 100*a* of the adapter 100 relative to the gripping portion 104. In such a configuration of the adapter 100, the gripping portion 104 may be adjacent a distal end or dispensing end of a syringe received within the syringe holder 108, which may facilitate inserting a needle end or dispensing end feature of the syringe into an object (e.g., a human, a non-human animal, a vial, and/or other object) and/or maintaining the dispensing end of the syringe in a position relative to the object, particularly when aspirating fluid into the syringe and/or dispensing fluid from the syringe.

As discussed above, in one example of using the adapter 100, the first grip portion 114 may be configured to receive a user's first digit. As shown in FIG. 6, the first grip portion 114 may include a first contour 130 that is configured to receive a user's first digit as it may be expected to be anatomically positioned when grasping or pinching an object between the first digit and another digit (e.g., a second digit of a user). However, such a contour is not required and contours may be provided for other purposes and/or may have different configurations.

Further, in some cases, the first grip portion 114 may be offset from the second grip portion 116, such that the first grip portion 114 and the second grip portion 116 are positioned relative to one another at positions where a first digit and a second digit (or other digit) of a user's hand would be expected to be located when the user is pinching or grasping an object with those digits. However, such a relative positioning is not required and the first grip portion 114 and the second grip portion 116 may be positioned relative to one another for one or more other purposes.

Figure 7:
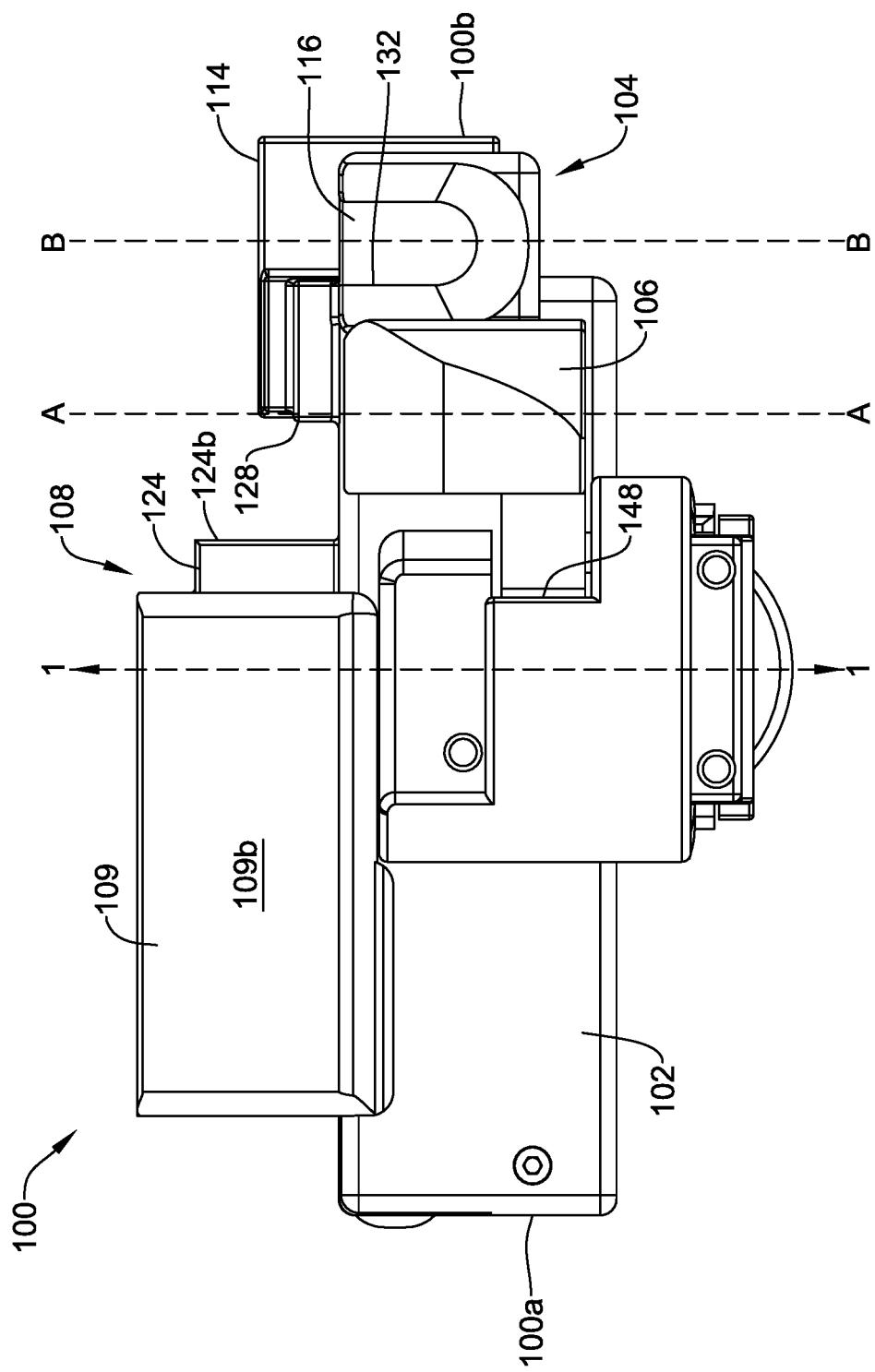
FIG. 7 is a second view of the example adapter of FIG. 5.

FIG. 7 is a bottom side view of the adapter 100. As can be seen in FIG. 7, the gripping portion 104 may be located at or adjacent the second end 100*b* of the adapter 100. Further, as depicted in FIG. 7, the actuator 106 may be at least partially spaced from and/or located toward the first end 100*a* of the adapter 100 relative to the gripping portion 104. In such a configuration of the adapter 100, the actuator 106 may be located at a location of the adapter 100 at which a user may be able to actuate the actuator 106 with one or more digits of the same hand holding the gripping portion 104 with one or more digits and/or having a palm engage the support portion 109 to aspirate and/or dispense fluid from a syringe received in the adapter 100.

As discussed above, in one example of using the adapter 100, the second grip portion 116 may be configured to receive a user's second digit. As shown in FIG. 7, the second grip portion 116 may include a second contour 132 that is configured to receive a user's second digit as it may be expected to be anatomically positioned when grasping or pinching an object between the first digit and second digit. However, such a contour is not required and contours may be provided for other purposes and/or may have different configurations.

Further, the actuator 106 may be at least partially longitudinally offset from the gripping portion 104. For example, such an offset configuration is depicted in FIG. 7 with dashed line A-A and dashed line B-B longitudinally offset from one another, where the line A-A extends through a center area of a grip surface of the actuator 106 and the line B-B extends through a center area of a grip surface of the gripping portion 104. The longitudinally offset position (e.g., proximal position) of the actuator 106 relative to a position of the gripping portion 104 may facilitate a user gripping or engaging the adapter 100 with one or more digits (e.g., at least two digits) to maintain control over a syringe received in the adapter 100 while aspirating fluid into or dispensing fluid from the syringe as a result of movement of one or more other digits on the same hand as the digit(s) gripping or engaging the adapter 100. In some cases, an offset distance between the actuator 106 and the gripping portion 104 be adjustable by adjusting a longitudinal position or other position of one or both of the actuator 106 and the gripping portion 104.

The actuator 106 may be adjusted (e.g., loaded and/or actuated) by moving the actuator 106 in a lateral direction about axis 1-1, as shown in FIG. 7. Alternatively or in addition, the actuator 106 may be linearly adjusted in a lateral direction relative to the gripping portion 104 and/or the syringe holder 108, and/or the actuator 106 may be adjusted in one or more other suitable manner (e.g., one or more other axes). In some cases, a palmar flexion movement of one or more digits of a user's hand may be used to adjust the actuator 106 about the axis 1-1 and/or in a linear manner, but other hand movements for adjusting the actuator 106 are contemplated. A palmar flexion movement may include moving the one or more digits toward a palm of the user's hand and such movement may utilize strong muscles of and/or around the user's hand.

As shown in FIG. 7, the adapter 100 may include a stop feature 148 (e.g., a portion of the housing 102 or other portion of the adapter 100). The stop feature 148 may limit movement of the actuator 106 about the axis 1-1 and/or in a linear direction. For example, the stop feature 148 or other stop feature may limit an amount of movement of the actuator 106 to less than about three hundred sixty (360) degrees around the axis 1-1, to less than about one hundred eighty (180) degrees around the axis 1-1, to less than about ninety (90) degrees around the axis 1-1, to less than about forty five (45) degrees around the axis 1-1, to less than about thirty (30) degrees around the axis 1-1, to less than about fifteen (15) degrees around the axis 1-1, and/or to a different amount of movement. In one example, the stop feature 148 or other stop feature may limit an amount of movement of the actuator 106 to less than about thirty degrees around the axis 1-1.

Figure 8:
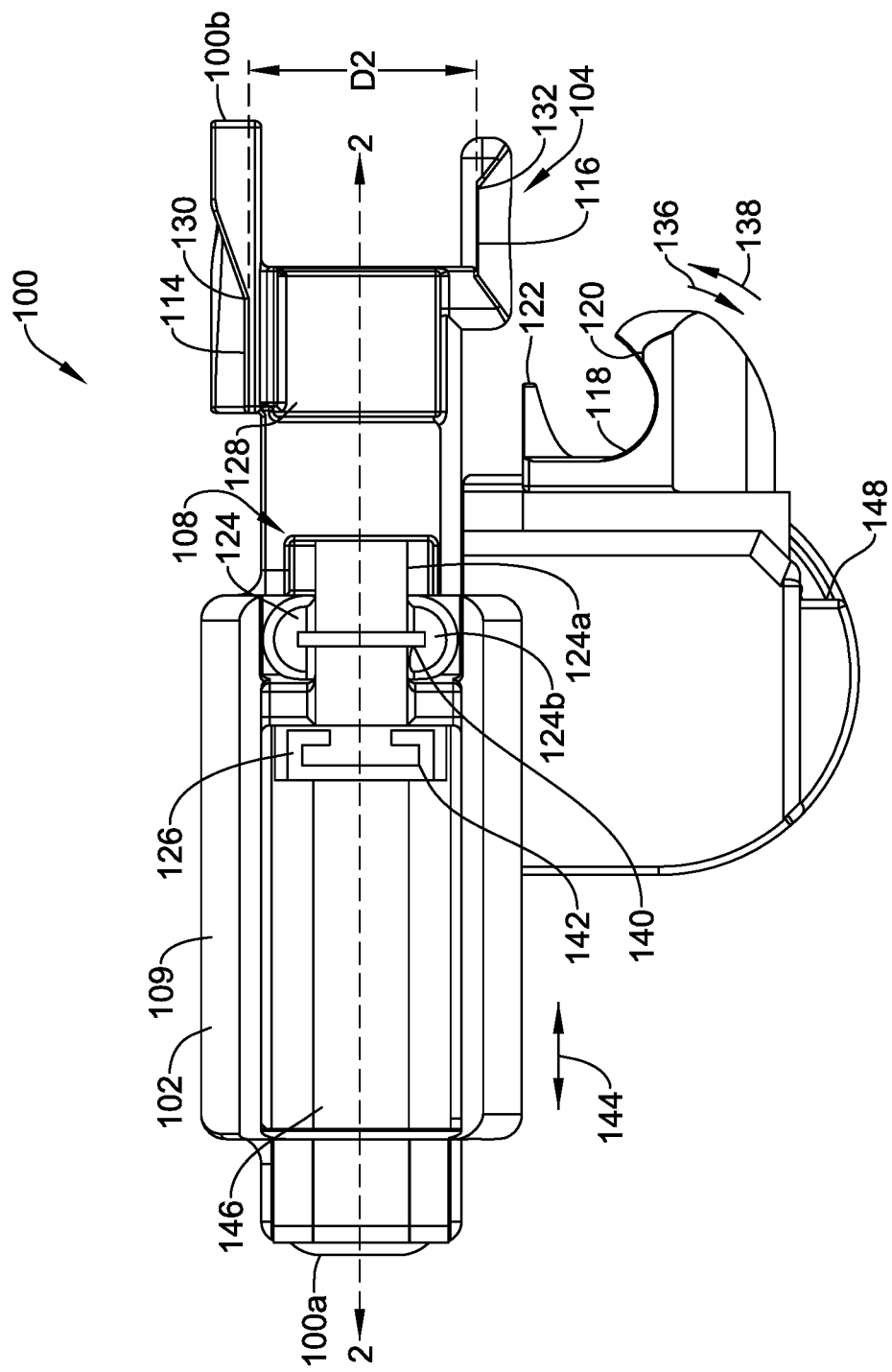
FIG. 8 is a third side view of the example adapter of FIG. 5.

FIG. 8 is a right side view of the adapter 100 when viewing the top view of the adapter 100 in FIG. 6 in a longitudinal direction from the first end 100a to the second end 100b. As depicted again in FIG. 8, the gripping portion 104 may be located at or adjacent the second end 100b of the adapter 100 and the actuator 106 may be at least partially spaced from and/or located toward the first end 100a of the adapter 100 relative to the gripping portion 104. Further, the fixed portion 124 and the adjustable portion 126 of the syringe holder 108, along with the syringe support 128 may extend along the housing 102 at locations extending toward the first end 100a of the adapter 100 relative to the gripping portion 104.

When the gripping portion 104 includes the first grip portion 114 and the second grip portion 116, as shown in FIG. 8, the first grip portion 114 and the second grip portion 116 may be laterally spaced from one another. In some cases, a surface of the first grip portion 114 configured to engage a user's digit and a surface of the second grip portion 116 configured to engage a user's digit may be spaced from one another a distance D2. The distance D2 may be configured to be less than, equal to, or greater than a distance D1 of a diameter of a syringe. When distance D1 of a diameter of a syringe is relatively small (e.g., a diameter of a barrel of a 3 milliliter (mL) syringe or other sized syringe), having a distance between gripping features greater than the distance D1 may reduce stress on a user's hand due to a wider grip than would be the case if the user were to be gripping the syringe having a diameter extending the smaller distance.

As can be seen in FIG. 8, the actuator 106 may include the grip portion 118. When a force is applied to the first support 120 of the grip portion 118 in a direction of arrow 136 or other direction, the actuator 106 may be loaded. Then, once the actuator 106 is loaded, a force may be applied against the second support 122 of the grip portion 118 in a direction of arrow 138 or other direction to actuate the actuator 106 and cause the adjustable portion 126 of the syringe holder 108 to positionally adjust along an axis 2-2 (as shown in FIG. 8) relative to the fixed portion 124 of the syringe holder 108. The directions of the arrows 136, 138 may be opposite lateral and/or rotational directions. Although the arrows 136, 138 are depicted with a rotational element, the direction of travel may be or may be at least partially linear. Further, it is contemplated that the actuator 106 may be alternatively configured to be actuated by applying a force to the second support 122 or other portion of the actuator 106.

The fixed portion 124 and the adjustable portion 126 of the syringe holder 108 may include one or more slots for receiving a flange or other portion of a syringe. For example, as shown in FIG. 8, the fixed portion 124 may include a barrel flange slot 140 for receiving a barrel flange and the adjustable portion 126 may include a plunger flange slot 142 for receiving a plunger flange. In some cases, the barrel flange slot 140 and/or the plunger flange slot 142 may be configured to create a friction fit or other engaging fit with a barrel flange or plunger flange, respectively, received therein. Additionally or alternatively, as discussed above, one or both of the barrel flange slot 140 and the plunger flange slot 142 may be configured to receive an insert (e.g., a sub-adapter), where the insert may have a slot configured to receive a flange of a syringe that is too small or too large to fit in one of the barrel flange slot 140 or the plunger flange slot 142. Use of an insert or other similar feature may facilitate using the adapter 100 with various sizes of syringes. Other mechanisms for attaching a syringe to the adapter 100 are contemplated including, but not limited to, a releasable locking mechanism.

The adjustable portion 126 of the syringe holder 108 may linearly adjust in the direction of arrows 144 in response to movement of the actuator 106 in the direction of arrow 138. Alternatively, or in addition, the adjustable portion 126 of the syringe holder 108 may be linearly adjustable in the direction of arrows 144 in response to movement of the actuator 106 in the direction of arrow 136. In some cases, the adjustable portion 126 may be adjusted in the directions of arrows 144 along a linear guide track 146. Alternatively, the adjustable portion 126 of the syringe holder 108 may not include the linear guide track 146 or may include a different guide track.

The adapter 100 may include one or more stops (not shown) to limit movement of the adjustable portion 126. For example, one or more stops may be placed along an adjustment path of the adjustable portion 126 (e.g., along a path following arrows 144 and/or other path) to limit and/or prevent movement of the adjustable portion 126 beyond the stops. In one example, a stop may be located adjacent to, but before, an end of the path of the adjustable portion 126 to prevent a plunger from completely withdrawing from a barrel of a syringe. Additionally, or alternatively, a stop may be provided along the path of the adjustable portion 126 to limit or prevent over insertion of a plunger into a barrel of the syringe. The stops may take any form and may be formed from and/or attached to the housing 102, the linear guide track 146, a linear guide 151 (discussed below with respect to FIG. 10), or other portion of the adapter 100 such that the stop(s) limit movement of the adjustable portion 126.

In some cases, the syringe holder 108 may utilize ball detents to facilitate positioning the adjustable portion 126 relative to the fixed portion 124. For example, a ball detent may be utilized to provide an audible and/or tactile indication of when the adjustable portion 126 is properly positioned, relative to the fixed portion, for loading a syringe.

Figure 9:
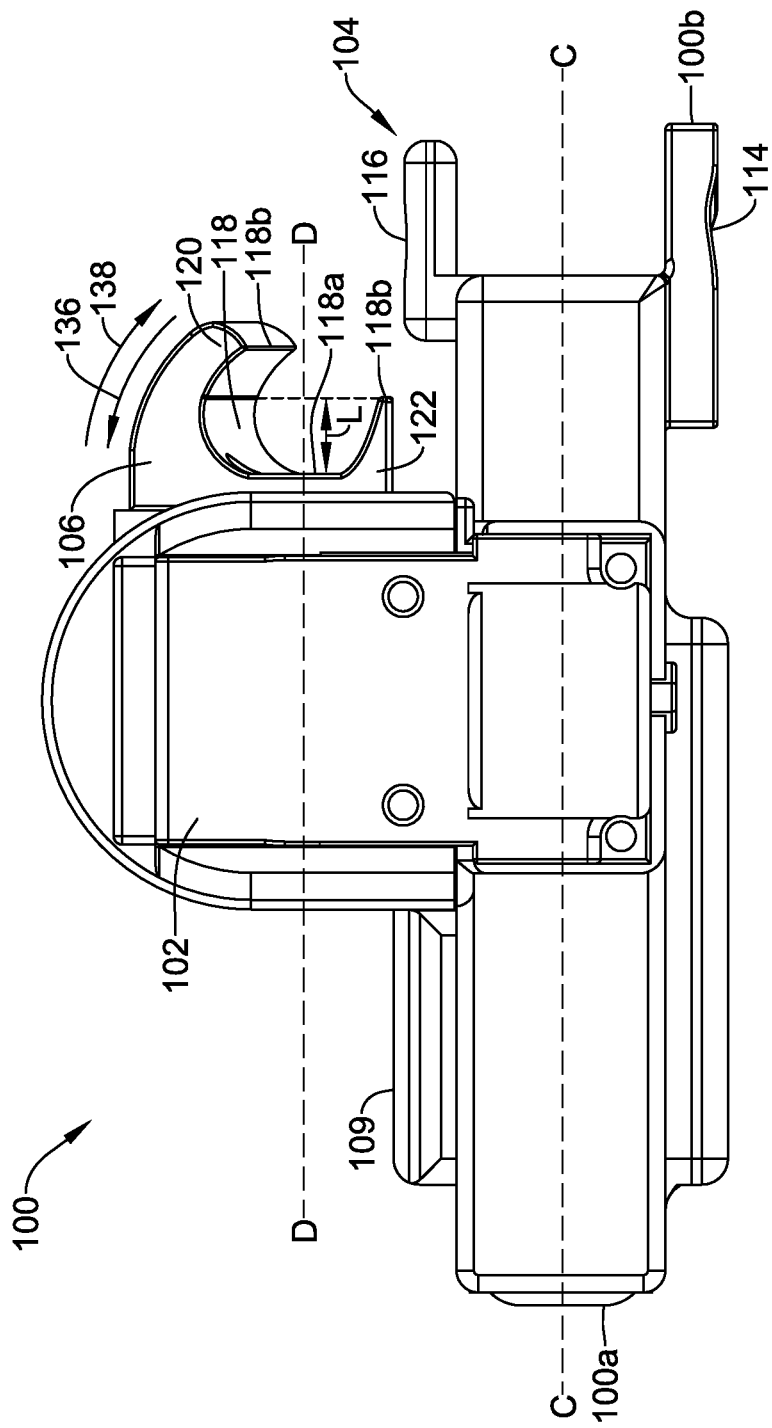
FIG. 9 is a fourth side view of the example adapter of FIG. 5.

FIG. 9 is a left side view of the adapter 100 when viewing the top view of the adapter 100 in FIG. 6 in a longitudinal direction from the first end 100a to the second end 100b. As depicted again in FIG. 9, the gripping portion 104 may be located at or adjacent the second end 100b of the adapter 100 and the actuator 106 may be at least partially spaced from and/or located toward the first end 100a of the adapter 100 relative to the gripping portion 104. Further, the actuator 106 may be at least partially laterally offset from the gripping portion 104. For example, such an offset configuration is depicted in FIG. 9 with dashed line C-C and dashed line D-D laterally offset from one another, where line C-C extends through a center of a width of the gripping portion 104 and line D-D extends through a center of a width of the actuator 106. In some cases, line C-C may correspond to axis 2-2, but this is not always required. The laterally offset and proximal position of the actuator 106 relative to the gripping portion 104 may facilitate a user gripping or engaging the adapter 100 with at least two digits to maintain control over a syringe received in the adapter while aspirating fluid into or dispensing fluid from the syringe with a palmar flexion motion or other motion of one or more other digits of the user's hand.

Further, as discussed above, the grip portion 118 of the actuator 106 may have a length configured to receive one or more digits of a user's hand. For example, the grip portion 118 may have any length L configured to receive at least part of a digit of a user's hand, where the length L may extend from a base 118a to a nearer end 118b of the first support 120 and the second support 122 to the base 118a, but this is not required. As shown in FIG. 9, the nearer end 118b may be an end of the second support 122. Example lengths L may include, but are not limited to, lengths from zero (0) centimeters (cm) to twenty (20) centimeters or longer. In one example, a grip portion 118 configured for a single digit may have a length L from about one (1) cm to about three (3) cm, a grip portion 118 configured for two digits may have a length L from about two (2) cm to about six (6) cm, and a grip portion 118 configured for three digits may have a length L from about three (3) cm to about nine (9) cm. These are just some examples and other lengths L, larger or smaller than the examples, may be utilized to configure the grip portion 118 for receiving one or more digits of a user's hand.

Figure 10:
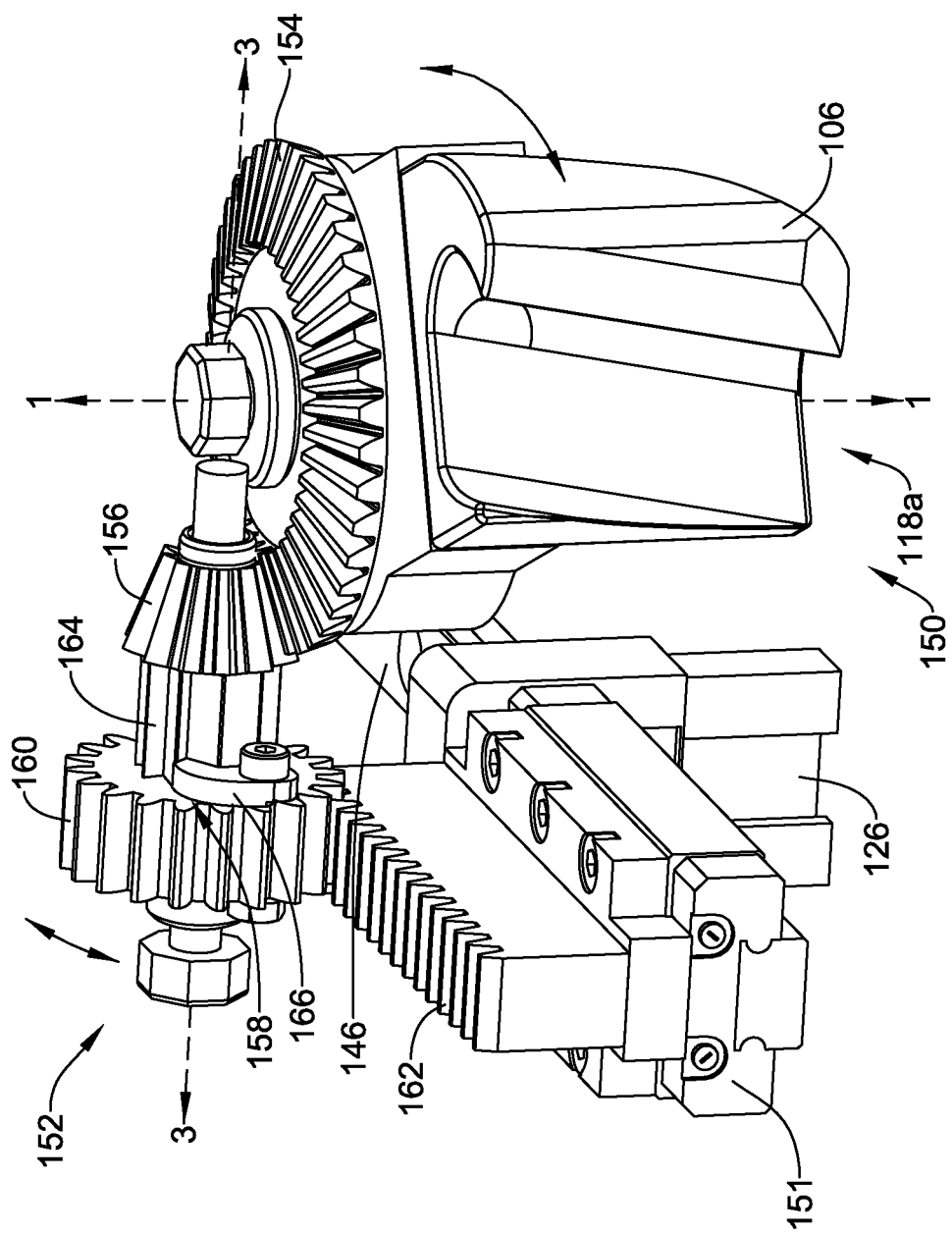
FIG. 10 is a perspective view of an example gear system of an adapter for use with a syringe.

FIG. 10 depicts the actuation system 150 of the adapter 100, which may be at least partially covered by the housing 102 (depicted in FIGS. 5-9). The actuation system 150 may include the actuator 106, the adjustable portion 126 of the syringe holder 108 (not shown in FIG. 10), the linear guide track 146, a linear guide 151, a gear system 152, and/or one or more other components. Although the actuation system 150 is depicted and described as having the gear system 152, it is contemplated that the actuation system 150 may include one or more additional or alternative suitable systems for causing movement of the adjustable portion 126 in response to movement of the actuator 106 including, but not limited to, a pneumatic system, a belt system, and/or other suitable system that may include different gears than what is discussed herein or no gears.

The gear system 152 may be secured or fixed relative to the housing 102, the gripping portion 104, the syringe holder 108, and/or one or more other components of the adapter 100. Further, the gear system 152 may be part of or in communication with the actuator 106 and the adjustable portion 126 of the syringe holder 108 to adjust or facilitate adjusting the adjustable portion 126 relative to the fixed portion 124 of the syringe holder 108 in response to actuation of the actuator 106. In some cases, the gear system 152 or a portion of the gear system 152 may be adjustable relative to the housing 102, the gripping portion 104, the syringe holder 108, the actuator 106, and/or one or more other components of the adapter 100 to facilitate configuring adapters 100 for different hand sizes of users. Additionally or alternatively, when the actuator 106 is elongated to facilitate receiving a plurality of digits and/or larger digits, the gear system 152 may be adjusted toward or located toward the first end 100a of the adapter 100 relative to what is depicted in the Figures, but this is not required.

The gear system 152 may include any number of drive or driven gears or gear components arranged in one or more configurations to transfer lateral motion (e.g., including linear and/or rotational motion) of the actuator 106 into longitudinal motion of the adjustable portion 126 of the syringe holder 108. As shown in FIG. 10, the drive or driven gears or gear components of the gear system 152 may include a drive gear 154, a drive pinion 156, a ratchet system 158, a driven pinion 160, and a rack 162. Other components (e.g., screws, shafts, bearings, belts, chains, springs, etc.) may be utilized as needed for connecting or operating the various depicted gear components and/or for other purposes.

The drive gear 154 may include teeth (e.g., helical teeth, spur teeth, etc.) configured to engage teeth (e.g., helical teeth, spur teeth, etc.) of the drive pinion 156. In some cases, the teeth of the drive gear 154 and the teeth of the drive pinion 156 may be angled or beveled to engage one another in response to rotation of the drive gear 154 and cause the drive pinion 156 to rotate about an axis 3-3 that may be perpendicular to the axis 1-1 about which the drive gear 154 may rotate. Alternatively, the drive pinion 156 may be configured to rotate about an axis that may be parallel to or at any other angle with respect to the axis 1-1 or other axis about which the drive gear 154 may rotate. The drive pinion 156 may be connected to and/or may be in communication with the ratchet system 158 such that the ratchet system 158 rotates with the drive pinion 156, but this is not required.

The drive gear 154 may rotate in response to movement of the actuator 106 (e.g., lateral linear and/or rotational movement of the actuator 106 to load and/or actuate the actuator 106). In some cases, the drive gear 154 may be formed with the actuator 106, the drive gear 154 may be connected to the actuator 106, and/or the drive gear 154 may be in communication with the actuator 106 through one or more other components.

The ratchet system 158 may include a ratchet gear 164, a pawl 166, a bias mechanism (not shown) configured to bias the pawl 166 toward teeth of the ratchet gear 164, and/or one or more other components. In some cases, the ratchet gear 164 may be formed with the drive pinion 156, but this is not required and the ratchet gear 164 may be a component that is separate from the drive pinion 156. The teeth of the ratchet gear 164 may be uniform, but asymmetrical, with each tooth having a moderate slope on one edge and a steeper slope on the other edge. Alternatively, the teeth of the ratchet gear 164 may be uniform and symmetrical. In operation, the pawl 166 of the ratchet system 158, which may be biased to engage teeth of the ratchet gear 164, may allow the ratchet gear 164 to rotate relatively freely in a first direction (e.g., the pawl 166 may slip over teeth of the ratchet gear 164), while providing more resistance against movement of the ratchet gear 164 (e.g., the pawl 166 may engage teeth of the ratchet gear 164) and moving with the ratchet gear 164 when the ratchet gear 164 rotates in a second direction opposite or substantially opposite the first direction.

As the pawl 166 slides over an edge of the teeth of the ratchet gear 164, the ratchet system 158 may make an audible indication (e.g., a click or other noise) and/or a tactile indication that the pawl 166 passed over a tooth of the ratchet gear 164. As a result, it may be possible to count the audible indications and/or tactile indications when loading the actuator 106 (and as a result the gear system 152) to determine a loading of the actuator 106 (e.g., a distance the adjustable portion 126 of the syringe holder 108 may move in response to actuation of the actuator 106). In one example, if it is known that each audible or tactile indication is equal to a received syringe aspirating or dispensing 1 mL of fluid or other predetermined amount of fluid, a user may calculate an amount of fluid that will be aspirated into or will be dispensed from the syringe in response to fully actuating the actuator 106 based on a number of audible and/or tactile indications that are identified when loading the actuator 106 and/or the gear system 152 from a fully actuated (e.g., unloaded position) to a desired loaded position.

The ratchet system 158 may be a unidirectional ratchet or the ratchet system 158 may be a reversible ratchet. When the ratchet system 158 is unidirectional, the gear system 152 may be able to drive the adjustable portion 126 of the syringe holder 108 in only a single direction. When the ratchet system 158 is reversible, the gear system 152 may be able to drive the adjustable portion 126 of the syringe holder 108 in two directions opposite or substantially opposite one another (e.g., in both directions along arrows 144 in FIG. 8).

Additionally or alternatively to the ratchet system 158 being reversible such that the gear system 152 may be able to drive the adjustable portion 126 of the syringe holder 108 in two directions opposite or substantially opposite one another, the adapter 100, the adapter 300 (discussed below), and/or other suitable adapters may be configured in one or more other manners to facilitate driving the adjustable portion 126 in two directions opposite or substantially opposite one another in response to actuation of an actuator. In one example, the gear system 152 may include additional and/or alternative gear components to facilitate driving the adjustable portion 126 in two opposite or substantially opposite directions. Further, in some cases, the actuator 106 may be adjustable (e.g., in an axial direction along axis 1-1 and/or adjustable in one or more other suitable directions) from a first position facilitating driving the adjustable portion 126 in a first direction (e.g., where the first position may result in the actuator 106 engaging gears or other suitable components that are configured to drive the adjustable portion 126 in the first direction) to a second position facilitating driving the adjustable portion 126 in a second direction opposite or substantially opposite the first direction (e.g., where the second position may result in the actuator 106 engaging gears or other suitable components that are configured to drive the adjustable portion 126 in the second direction). Other suitable configurations of the adapter 100, the adapter 300 (discussed below), and other suitable adapters are contemplated for providing two-direction adjustment of the adjustable portion thereof to drive a syringe plunger in two directions (e.g., an aspirating direction and a dispensing direction).

Further, the pawl 166 of the ratchet system 158 may be secured to or may otherwise be in communication with the driven pinion 160. In one example, the pawl 166 may be secured to the driven pinion 160 at a location adjacent a side wall of the driven pinion 160 with a pin or other element that may extend through the pawl 166 and the side wall of the driven pinion 160 such that the pawl 166 may be rotatable about the pin or other element. Other configurations may be utilized to secure the pawl 166 relative to the driven pinion 160. The pawl 166 secured to or in communication with the driven pinion 160 may facilitate rotation of the driven pinion 160 in response to and in a direction of movement of the pawl 166 and the ratchet gear 164 about axis 3-3. As the driven pinion 160 rotates, teeth (e.g., helical teeth, spur teeth, etc.) of the driven pinion 160 may engage teeth (e.g., helical teeth, spur teeth, etc.) of the rack 162 and cause the rack 162 to translate longitudinally.

The rack 162 of the gear system 152 may be connected to and/or in communication with (e.g., secured to or secured relative to) the adjustable portion 126 of the syringe holder 108. As such, the adjustable portion 126 of the syringe holder 108 may be longitudinally adjusted with respect to the fixed portion 124 of the syringe holder 108 in response to longitudinal adjustment of the rack 162. Further, as shown in FIG. 10, the rack 162 may be secured to a linear guide 151 which is configured to adjust along the linear guide track 146 and ensure the rack 162 and the adjustable portion 126 of the syringe holder 108 may be longitudinally adjusted in a linear and consistent manner.

In some cases, the actuation system 150 of the adapter 100 may include a power assist that assists a user in actuating the actuator 106. The power assist may facilitate reducing an amount of force required to drive the syringe plunger, while still providing feedback to a user. In some cases, the power assist may sense actuation of the actuator 106 and initiate an actuation assist to reduce the amount of force a user is required to apply to the actuator 106 to drive the plunger. The power assist may be a mechanical assist, an electromechanical assist, and/or other suitable type of power assist.

Figure 11:
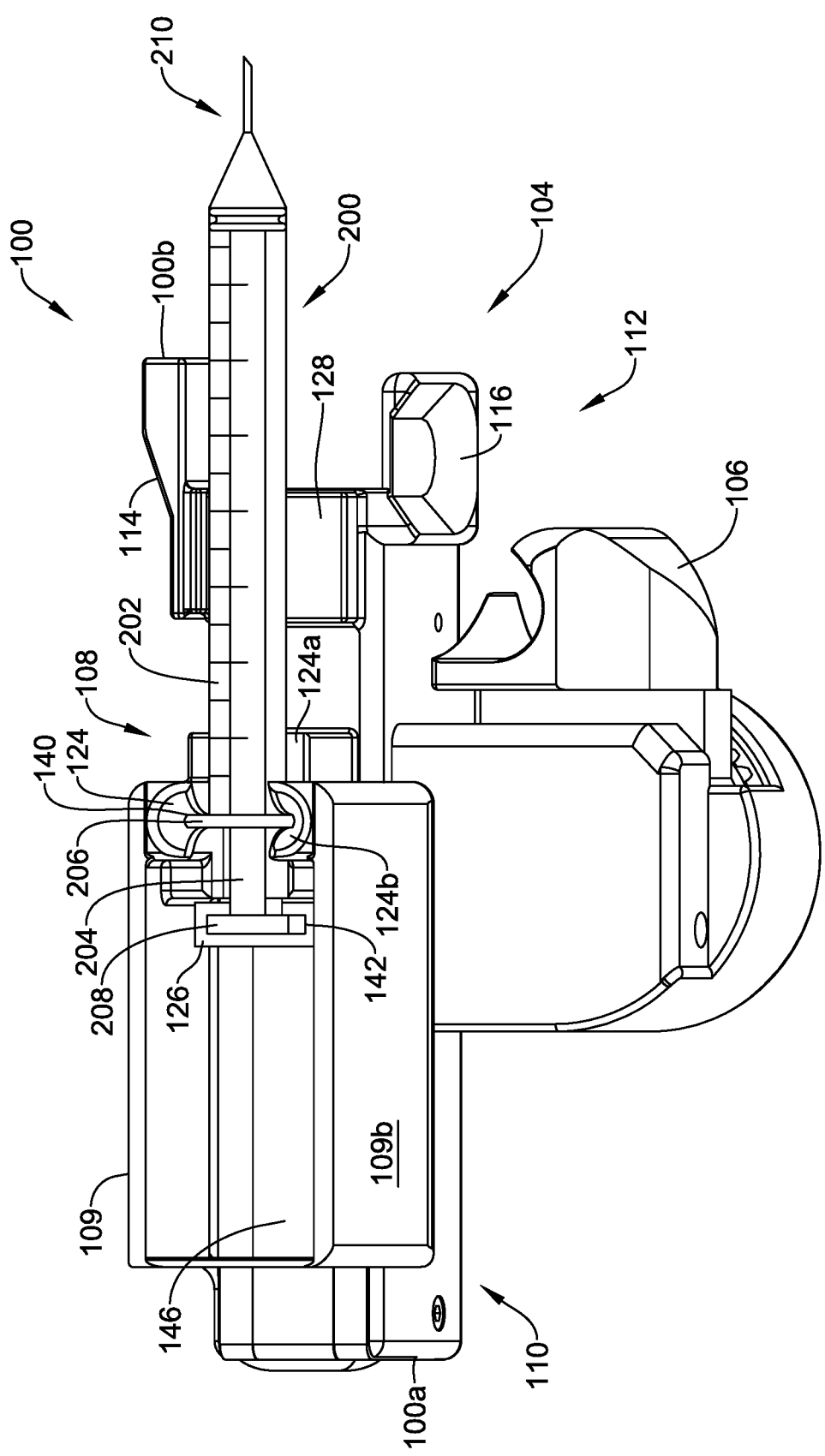
FIGS. 11-13 are side perspective views of an example adapter with a received syringe depicting an aspirating technique.
Figure 12:
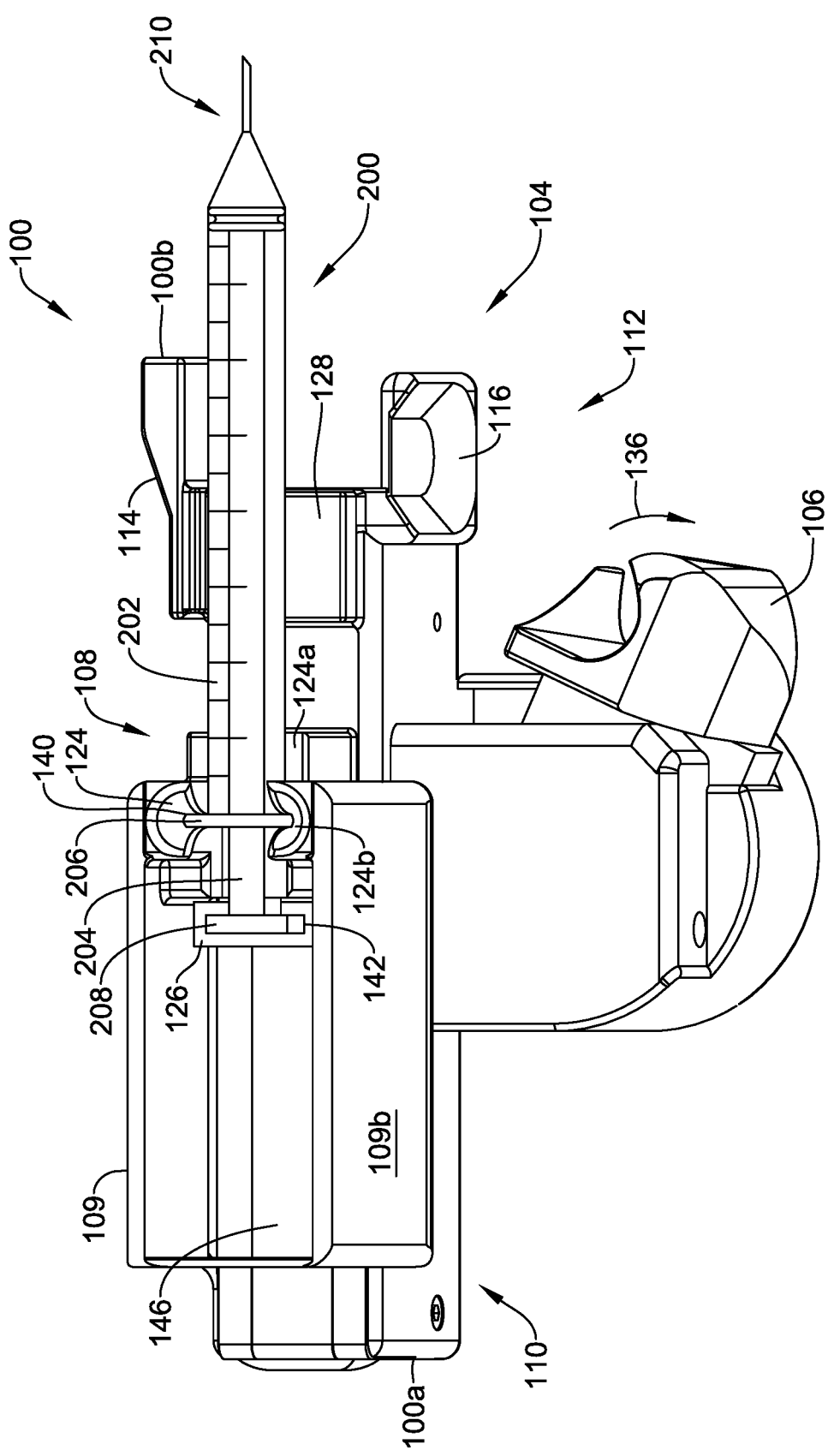
Figure 13:
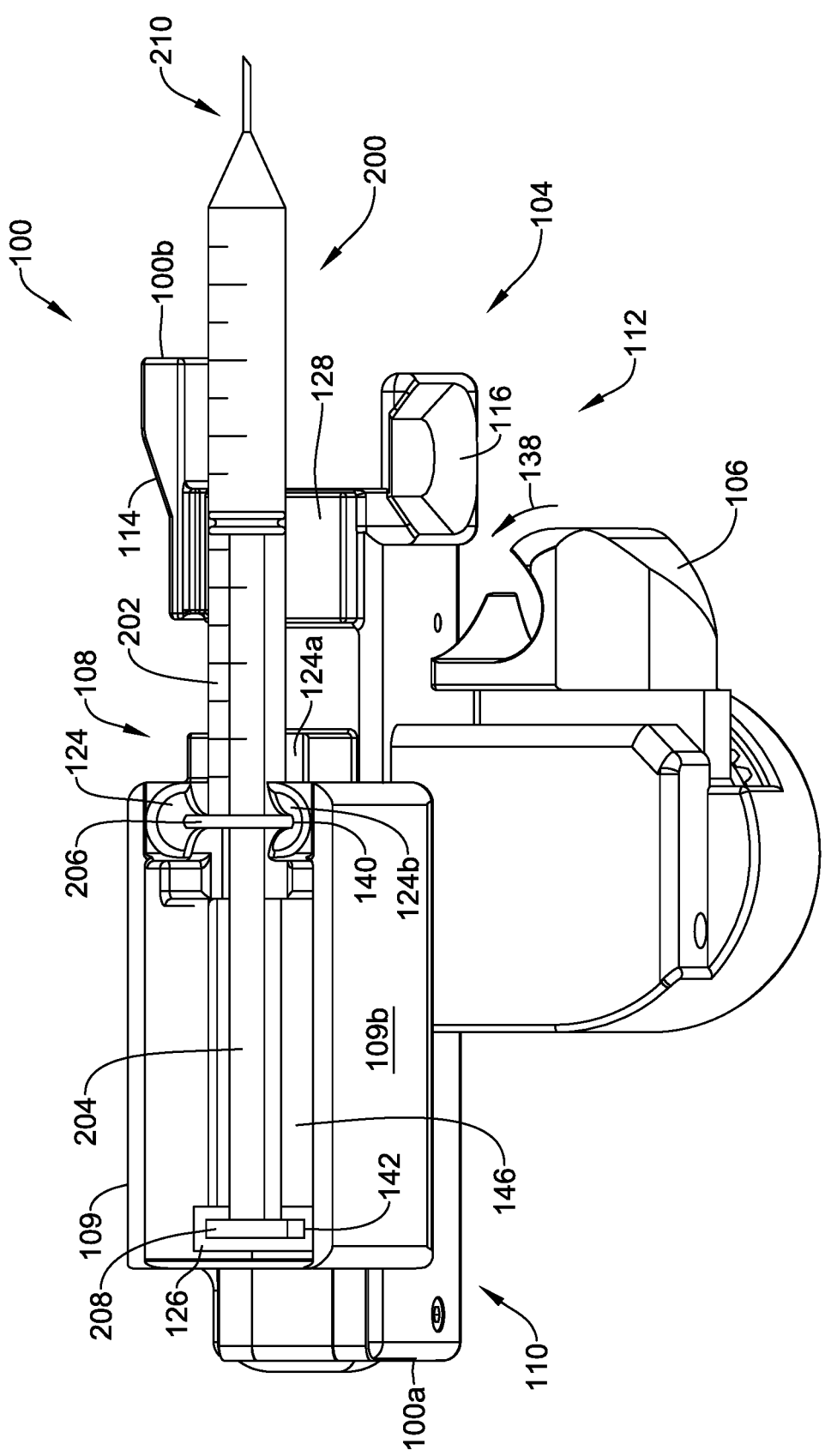

FIGS. 11-13 depict steps in a technique for loading and actuating an actuator to aspirate fluid into a syringe received within the adapter 100. A similar technique may be utilized for dispensing fluid.

FIG. 11 depicts the adapter 100 with a syringe 200 received in the fixed portion 124 and the adjustable portion 126 of the syringe holder 108 and a flange 206 of a barrel 202 within the barrel flange slot 140 and a flange 208 of a plunger 204 in the plunger flange slot 142. Additionally, the barrel 202 of the syringe 200 may be supported by the syringe support 128 and a dispensing end 210 of the syringe 200 may extend past or distal of the gripping portion 104. The actuator 106 in FIG. 11 is in an unloaded position and the adjustable portion 126 of the syringe holder 108 is maintaining the plunger 204 in a fully inserted position within the barrel 202.

FIG. 12 depicts the adapter 100 and the syringe 200 in a similar configuration to that of FIG. 11, except that actuator 106 has been laterally adjusted (e.g., in a first direction of the arrow 136) away from the gripping portion 104 and/or the syringe holder 108 to a loaded position. While translating the actuator 106 (and as a result the gear system 152) to the loaded position depicted in FIG. 12, a user may count a number of audible and/or tactile indications to determine an amount fluid that will be aspirated in response to fully actuating the actuator 106 starting at the loaded position. When a gear system 152 does not include a ratchet that provides audible and/or tactile indications and/or in other situations, other indicator systems may be used to indicate an amount of fluid that will be aspirated or dispensed in response to actuating the actuator 106. Other indicator systems may include, but are not limited to, other tactile systems, other audible systems, measurement indicia on or adjacent the actuator 106 and/or the housing 102 adjacent the actuator 106, and/or one or more other indicator systems. Once the actuator 106 is adjusted to a desired load position, the actuator 106 may be ready for actuation.

FIG. 13 depicts the adapter 100 in an actuated configuration and the syringe 200 in a fully aspirated configuration. After loading the actuator 106, the actuator 106 may be fully actuated by laterally adjusting (e.g., in a second direction of the arrow 138) the actuator 106 toward the gripping portion 104 and/or the syringe holder 108 to an actuated position. Actuating the actuator 106 may cause the plunger 204 to withdraw from the barrel 202 of the syringe 200 in response to the gear system 152 (not shown in FIG. 13) causing the adjustable portion 126 of the syringe holder 108 to adjust along the linear guide track 146. In one example of actuating the actuator 106, a palmar flexion movement of one or more digits of a user's hand may be utilized to adjust the actuator 106 from a loaded position to an actuated position and adjust a position of the adjustable portion 126 of the syringe holder 108 relative to the fixed portion 124 of the syringe holder 108. Such a palmar flexion movement of one or more digits of a user's hand may be formed while two or more other digits and/or a palm of the user's hand are engaged with the adapter 100 (e.g., the gripping portion 104 of the adapter 100). Once a fluid has been aspirated into the syringe 200, the syringe 200 may be removed from the adapter 100 or the fluid in the syringe 20 may be dispensed from the syringe 200 using the adapter 100 or in one or more other manners.

As mentioned above, FIGS. 14-21 depict various features of syringe attachment devices or adapters in the context of the illustrative syringe attachment device or adapter 300. The adapter 300 may include features that are similar to features of the adapter 100 described above and/or additional or alternative features to the features of the adapter 100. Although such details of features may not be particularly discussed with respect to the adapter 300 or the adapter 100, respectively, the details of features discussed with respect to the adapter 100 may be additionally or alternatively incorporated into the adapter 300 and the details of features discussed with respect to the adapter 300 may be additionally or alternatively incorporated into the adapter 100.

Figure 14:
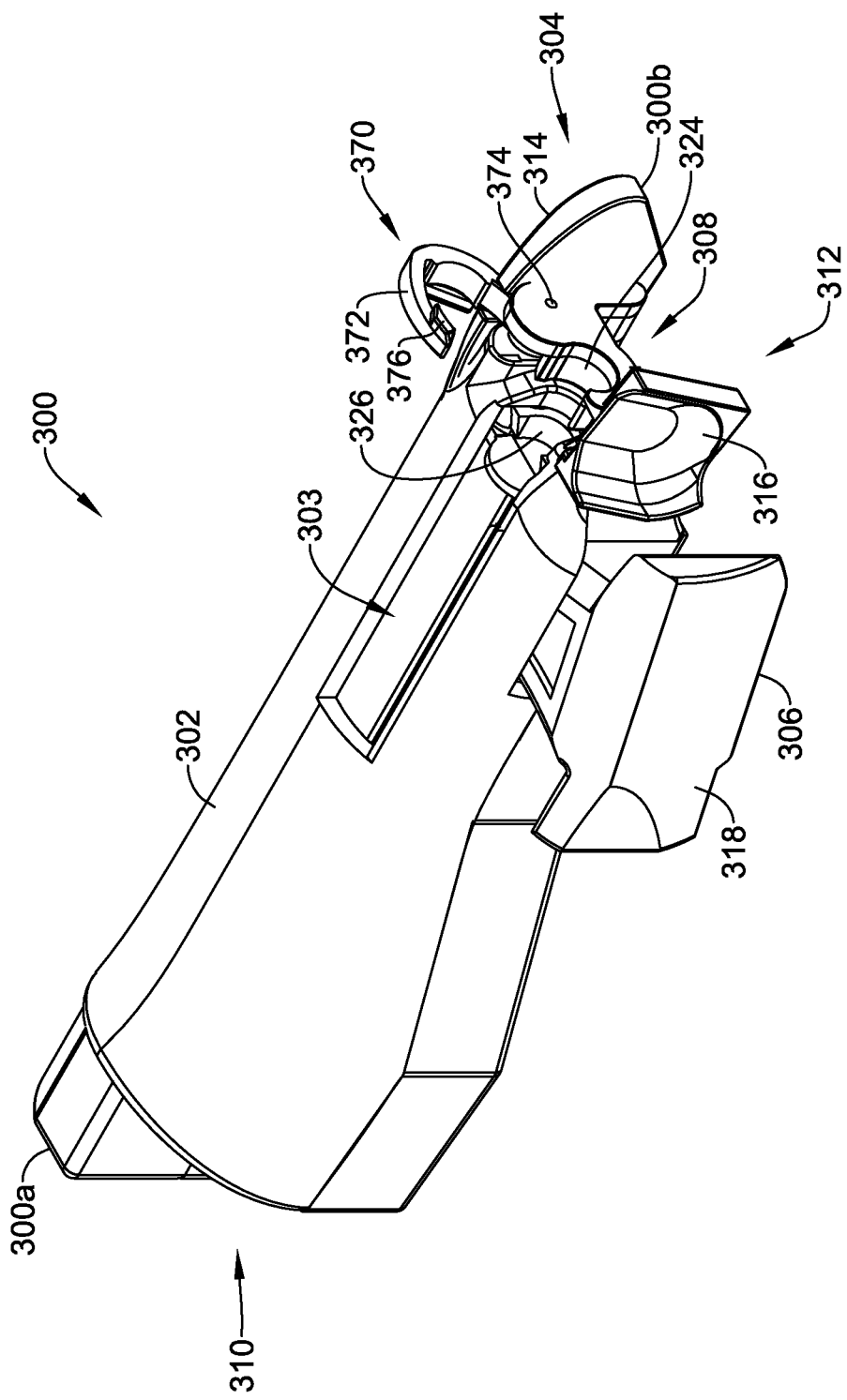
FIG. 14 is a perspective view of an example adapter for use with a syringe, as seen from a bottom of the example adapter.

FIG. 14 is a perspective view of the illustrative adapter 300 configured to be used with a syringe (e.g., the syringe 2 or other syringe). In some cases, the adapter 300 may include a housing 302, a gripping portion 304, an actuator 306, and a syringe holder 308, among other features or components. One or more of the housing 302, the gripping portion 304, the actuator 306, the syringe holder 308, and/or other components of the adapter 300 may form a body of the adapter 300. The body of the adapter 300 may have a first end portion 310 adjacent a first end 300a of the adapter 300 and a second end portion 312 adjacent a second end 300b of the adapter 300 opposite the first end 300a.

The housing 302 may at least partially cover one or more components of the adapter 300. In one example, the housing 302 may at least partially cover an actuation system (e.g., an actuation system 350, discussed in greater detail below, or other suitable actuation systems) of the adapter 300. The housing 302 may include one or more slots or openings 303 configured to provide access for receiving a syringe in the adapter 300, removing the syringe from the adapter 300, and/or for one or more other suitable purposes. Further, in some cases, the housing 302 may at least partially form one or more features of the adapter 300 including, but not limited to, the gripping portion 304, the actuator 306, the syringe holder 308, and/or other features of the adapter 300. In some cases, the housing 302 may be omitted and/or entirely formed from other components of the adapter 300.

The gripping portion 304 may be located adjacent to the second end portion 312 of the body of the adapter 300. The gripping portion 304 may be configured in a manner similar to how the gripping portion 104 of the adapter 100 is configured, but this is not required.

The gripping portion 304 may be any portion of the adapter 300 configured to allow a user to grip or otherwise engage the adapter 300 with one or more digits. In one example, the gripping portion 304 may be configured to allow a user to apply a pinching force to the gripping portion 304 to steadily hold or grasp the adapter 300. Structurally, in some cases, the gripping portion 304 may be or may include extensions (e.g., flanges or other extensions) of or extending from the housing 302, that may be, or may be formed in, sides of the housing 302 (e.g., opposing sides of the housing 302 or other sides of the housing 302), and/or may include one or more other features of or extending from the body of the adapter 300.

The gripping portion 304 may include a first grip portion 314 and a second grip portion 316. Alternatively, the gripping portion 304 may include a single grip portion or more than two grip portions. The first grip portion 314 and the second grip portion 316 may be configured to receive one or more digits of a user. In one example, the first grip portion 314 may be configured to receive an initial digit of a user (e.g., a user's first digit 18 or other digit) and the second grip portion 316 may be configured to receive another digit of the user (e.g., the user's second digit 20 or other digit). When a user is gripping the gripping portion 304 with two digits in the manner of the example, a palm of the hand with which the user is gripping the gripping portion 304 may be facing the body of the adapter 300 and disposed toward the first end portion 310 relative to the portions of the user's digits gripping the gripping portion 304.

In some cases, portions of the gripping portion 304 may include one or more gripping features. For example, the first grip portion 314 and/or the second grip portion 316 may be or may have indents, contours, bumps, lines, smooth surfaces, and/or other gripping features to facilitate receiving one or more digits of a user. Alternatively or in addition, one or more of the grip portions 314, 316 may not have any gripping features.

The actuator 306 may be part of or may be in communication with the actuation system of the adapter 300. Further, the actuation system may comprise a gear system (e.g., a gear system 352, discussed below with respect to FIG. 17) and/or one or more other actuation sub-systems (e.g., pneumatic, hydraulic, pulley, or other suitable actuation sub-system) configured to adjust a portion of the syringe holder 308 (discussed in greater detail below). In some cases, the actuator 306 may be in communication with an actuation sub-system at least partially within the housing 302 and/or may extend out of the housing 302 to be accessible by a user from exterior of the housing.

The actuator 306 may be or may include a grip portion 318 (e.g., a third grip portion) configured to receive one or more digits or a palm of a user's hand such that the one or more digits or palm of a user's hand may apply a force to the actuator 306 via a palmar flexion or other movement of the user. In operation, the actuator 306 may be entirely or at least partially automatically loaded in response to a force from a bias mechanism (e.g., the bias mechanism 347 discussed in greater detail below) in a first direction (e.g., a laterally outward direction) relative to the housing 302 and actuated in response to a force from the user acting on the grip portion 318 in a second direction (e.g., a laterally inward direction) opposed to the force from the bias mechanism. Alternatively or in addition, one or more portions of the grip portion 318 may be engaged by one or more digits or other portions of a hand of a user in one or more suitable manners other than during laterally inward or outward motions relative to the housing 302, the gripping portion 304, and/or the syringe holder 308 to drive a portion of the syringe holder 308. Movement of the actuator 306 (e.g., loading and actuating the actuator 306 or the actuation system) will be described in greater detail below.

The grip portion 318 of the actuator 306 may be configured to receive one or more digits of a user. As shown in FIG. 14, the grip portion 318 of the actuator 306 may be elongated (e.g., paddle-like) and configured to receive a palm and/or a plurality of digits of a user. Alternatively, the actuator 306 may be configured to receive a single digit or only a palm of a user. To facilitate receiving one or more of various portions of a user's hand, at least part of the actuation system of the adapter 300 may be adjusted toward the first end 300a of the adapter 300, adjusted toward the second end 300b of the adapter 300, shortened along a length of the adapter 300, and/or elongated along the length of the adapter 300. Although the adapter 300 may be configured to easily allow a user to aspirate fluid into a syringe and/or dispense fluid from the syringe by engaging the actuator 306 with a single digit, having an actuator 306 that may accept a plurality of digits and/or a palm may further reduce stress on a user's hand, wrist, and/or forearm areas in response to actuating the actuator 306.

In some cases, the grip portion 318 of the actuator 306 may be angled to facilitate a user actuating the actuator 306. In one example, the grip portion 318 may be angled about fifteen (15) degrees relative to a longitudinal axis of the adapter 300. Such an angle may facilitate actuation of the actuator 306 in a biomechanically efficient manner. Other angles of the grip portion 318 are contemplated. For example, the angle of the grip portion 318 may be different if a user's first digit is intended to actuate the actuator 306 than if a user's third digit is intended to actuate the actuator 306, but this is just an example and is not required.

Similar to the grip portions 114, 116, 118, the grip portions 314, 316, 318 may be configured in any suitable manner. In some cases, the grip portions 314, 316, 318 may be sides of the gripping portion 304 or the actuator 306, respectively. Alternatively or in addition, the grip portions 314, 316, 318 may be or may include one or more surfaces (e.g., surfaces with grip features such as indents, protrusions, bumps, recesses, and/or other suitable grip features), one or more flanges, one or more supports, or other suitable structure configured to facilitate maintaining a grip when engaging the gripping portion 304 and/or the actuator 306.

The syringe holder 308 may be at least partially formed from and/or may extend from the housing 302 at a location between the first end 300a and the second end 300b of the adapter 300, where the first end 300a and the second end 300b may be defined by the syringe holder 308 and/or other suitable portion of the adapter 300. The syringe holder 308 may be located along a length of the adapter 300 such that when a syringe is received within the syringe holder 308, an object engaging end or dispensing end of the syringe extends distally of the second end 100b of the adapter 300 (e.g., see FIGS. 18-20, discussed below).

The syringe holder 308 may include, among other components, a fixed portion 324 (e.g., a fixed first portion) and an adjustable portion 326 (e.g., an adjustable second portion), among other components. The fixed portion 324 of the syringe holder 308 may be configured to receive a barrel (e.g., the barrel 4 or other barrel of a syringe), a barrel flange (e.g., the barrel flange 14 or other barrel flange of a syringe), and/or one or more other portion of a barrel of a syringe. The adjustable portion 326 of the syringe holder 308 may be configured to receive a plunger flange (e.g., the plunger flange 16 or other plunger flange of a syringe), a plunger stem, and/or other portion of a plunger of a syringe. The components of the syringe holder 308 may be adjustable or otherwise configured to receive different sizes of syringes. In some cases, the fixed portion 324 and the adjustable portion 326 may be configured in a manner similar to how the fixed portion 124 and the adjustable portion 126 of the adapter 100 are configured, but this is not required.

The fixed portion 324 of the syringe holder 308 may be formed from one or more components and may be rigidly fixed or fixedly adjustable relative to the housing 302 and/or the gripping portion 304. In one example, a distance between the fixed portion 324 and the gripping portion 304 may be adjustable to facilitate receiving different lengths of syringes, but this is not required and the fixed portion 324 may be rigidly fixed with respect to the housing 302, the gripping portion 304, and/or one or more other components of the adapter 300.

The adjustable portion 326 of the syringe holder 308 may be formed from one or more components and may be in communication with the actuation system of the adapter 300. In some cases, the adjustable portion 326 may be axially and/or longitudinally adjustable relative to the fixed portion 324 of the syringe holder 308. As the adjustable portion 326 may be configured to receive and/or engage a plunger of a syringe, adjusting the adjustable portion 326 of the syringe holder 308 may result in aspirating fluid into the syringe and/or dispensing fluid from the syringe.

The fixed portion 324 and/or the adjustable portion 326 may be configured to secure the syringe in the syringe holder 308 via a friction fit, a snap fit, and/or through other securing mechanisms. In some cases, the fixed portion 324 and/or the adjustable portion 326 may include adjustable components that are adjustable to facilitate different sizes of syringes. In one example, one or more of the fixed portion 324 and the adjustable portion 326 may include one or more inserts or sub-adapters for accommodating and/or securing different sizes of plunger flanges, barrel flanges, or other components of a syringe within the syringe holder 308. Such inserts or sub-adapters may be releasably connected to and/or positioned within the syringe holder 308.

In some cases, the adapter 300 may include a locking mechanism 370 configured to releasably engage a syringe received within the adapter 300 and facilitate maintaining the syringe within the adapter 300. In the example of the locking mechanism 370 that is depicted in FIG. 14, the locking mechanism 370 may include a locking arm 372 configured to rotate about a pivot pin 374 (although the pivot pin 374 is depicted in FIG. 14, it is contemplated that the pivot pin 374 or a pivot point may not be viewable from exterior the housing 302 and/or may be viewable in one or more other locations than what is depicted in FIG. 14), engage a syringe received within the adapter 300, and lock the received syringe in the adapter 300. The locking arm 372 may include a protrusion 376 configured to engage the housing 302 of the adapter 300 in a snap fit or other type of connection (e.g., engage an opening through the housing 302 and/or otherwise engage the housing 302 to connect thereto). When the protrusion 376 is engaging the housing 302 (e.g., when the locking mechanism 370 is in a locked position), applying a force on the locking arm 372 may facilitate disengaging the protrusion 376 from the housing 302 to allow for a release of the locking arm 372 and removal of the syringe from the adapter 300. Although the locking mechanism 370 is described herein with respect to the locking arm 372 and the protrusion 376, other suitable locking mechanisms may be utilized, the locking mechanism 370 may be configured in one or more other manners to facilitate securing a syringe in the adapter 300, and/or the locking mechanism 370 may include one or more additional and/or alternative components (e.g., cams, slide mechanisms, forked mechanisms, and/or other suitable locking components).

Figure 15:
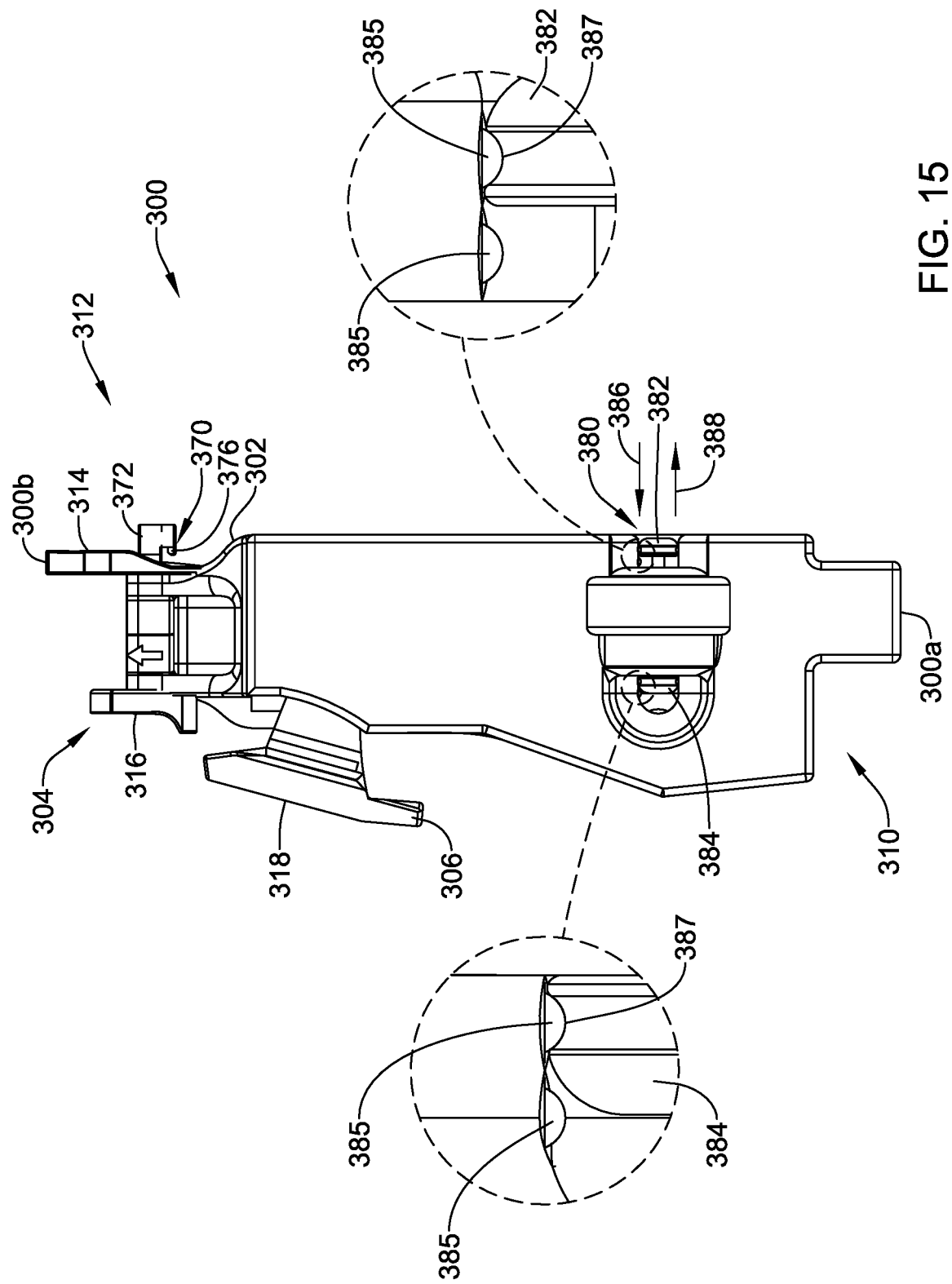
FIG. 15 is a side view of the example adapter of FIG. 14.

FIG. 15 is a side view of the adapter 300. Similar to as discussed with respect to the adapter 100 and as depicted in FIG. 15, the actuator 306 may be at least partially laterally and/or longitudinally offset from the gripping portion 304.

As can be seen in FIG. 15, the adapter 300 may include a selector 380. The selector 380 may be adjustable to facilitate engaging the actuator 306 with the adjustable portion 326 of the syringe holder 308 such that actuation of the actuator 306 (e.g., about an actuator axis or other suitable axis) adjusts a position of the adjustable portion 326 of the syringe holder 308 and disengaging the actuator 306 from the adjustable portion 326 such that the adjustable portion 326 may be freely adjustable relative to the fixed portion 324 of the syringe holder 308.

In the example of the selector 380 depicted in the Figures, the selector 380 may have a first selector element 382 (e.g., a first button or other suitable first selector) and a second selector element 384 (e.g., a second button or other suitable second selector). As an alternative to the selector 380 including the two selector elements 382, 384, the selector 380 may include a single selector or more than two selectors.

When the first selector element 382 is actuated in a direction of arrow 386, the selector 380 may disengage the actuator 306 from the adjustable portion 326 of the syringe holder 308. In some cases, actuating the first selector element 382 in the direction of the arrow 386 may cause the second selector element 384 to move in the direction of the arrow 386 with the first selector element 382, but this is not required. When the second selector element 384 is actuated in a direction of arrow 388, the selector 380 may engage the actuator 306 with the adjustable portion 326 of the syringe holder 308 such that actuation of the actuator 306 may cause movement of the adjustable portion 326. In some cases, actuating the second selector element 384 in the direction of the arrow 388 may cause the first selector element 382 to move in the direction of the arrow 388 with the second selector element 384. Although the selector 380 is described as being adjustable in the directions of arrows 386 and 388, the selector 380 may be adjustable in one or more other suitable directions to engage or disengage the actuator 306 with the adjustable portion 326. In one example, the selector 380 may be adjustable in a direction generally parallel to or collinear with an axis about which the drive pinion 356 and/or the driven pinion 360 rotate regardless of a direction of that axis and/or may be adjustable in one or more other suitable directions.

Figure 16:
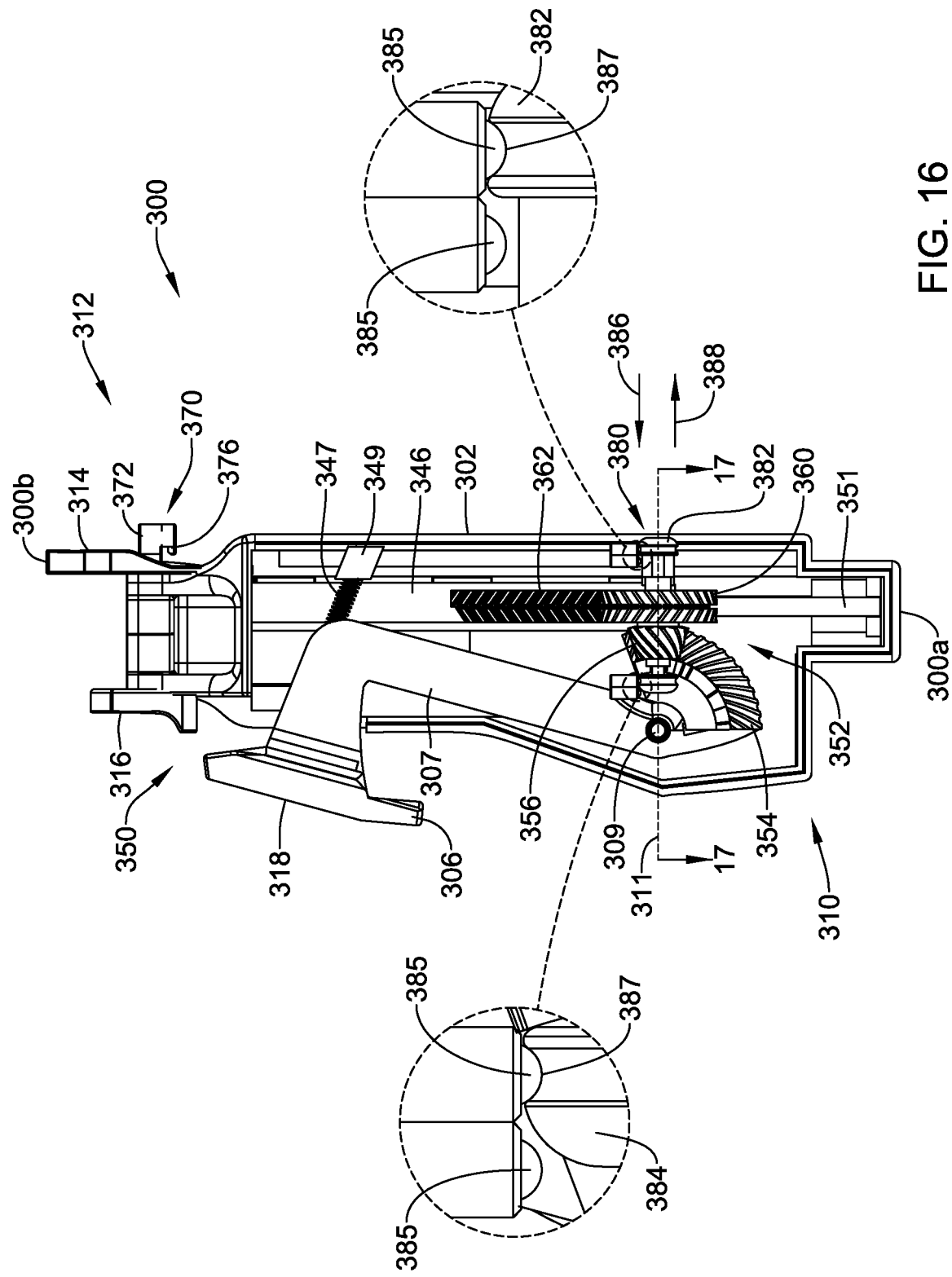
FIG. 16 is the side view depicted in FIG. 15, but with a portion of a housing of the example adapter removed.

The selector 380 may have one or more ball detents 385 configured to engage and/or disengage the first selector element 382 and/or the second selector element 384, as shown in FIGS. 15 and 16, to provide audible and/or tactile feedback when adjusting the selector 380. In some cases, a ball detent 385 may slide into one or more grooves 387 on the selector 380 as the selector 380 is adjusted in the direction of the arrows 386, 388 or in one or more other suitable directions to provide audible and/or tactile feedback to a user of proper adjustment of the selector 380. Additionally or alternatively, the adapter 300 may include one or more suitable indicators other than ball detents that provide audible and/or tactile feedback when adjusting the selector 380.

FIG. 16 is the side view of the adapter 300 depicted in FIG. 15, but with a portion of the housing 302 removed. With the portion of the housing 302 removed, it may be possible to view various components of the actuation system 350 that reside within the housing 302 including, but not limited to, portions of the actuator 306. The actuation system 350 may include, among other features, the actuator 306, an arm 307, the adjustable portion 326 of the syringe holder 308 (not shown in FIG. 16), a linear guide track 346, a linear guide 351, a gear system 352, and/or one or more other suitable components. For example, FIG. 16 depicts the actuator 306 having the arm 307 extending in a direction of the first end 300a of the adapter 300 to and/or beyond a pivot point 309 (e.g., a pivot point at a pin) at an axis that extends out of and/or through the paper on which FIG. 16 is depicted. The arm 307 may engage or may be configured to engage the gear system 352 such that movement of the actuator 306 may cause movement of the adjustable portion 326 of the syringe holder 308. In some cases, an elongated arm 307, as depicted in FIG. 16, may facilitate reducing a force from a user's hand that is required to actuate the actuator 306 and thus, mitigate repetitive use injuries due to prolonged use of the adapter 300.

The gear system 352 may include any number of drive or driven gears or gear components arranged in one or more configurations to transfer lateral motion (e.g., including linear and/or rotational motion) of the actuator 306 into longitudinal motion of the adjustable portion 326 of the syringe holder 308. The drive or driven gears or gear components of the gear system 352 may include a drive gear 354, a drive pinion 356, a ratchet system 358 (see FIG. 17), a driven pinion 360, and a rack 362. Other components (e.g., screws, shafts, bearings, belts, chains, springs, etc.) may be utilized as needed for connecting or operating the various depicted gear components and/or for other purposes.

A force applied to the actuator 306 may act against a force from the bias mechanism 347 (e.g., a spring or other suitable bias mechanism). The bias mechanism 347 may be configured to act on the actuator 306 to load the actuator 306 once an actuating force (e.g., a force greater than a force applied to the actuator 306 by the bias mechanism 347) has been removed from the actuator. Such a configuration may allow for automatic loading of the actuator 306 rather than requiring a user to load the actuation system 350 by manually moving the actuator 306 in a direction opposite of a direction the actuator 306 may be moved as it is actuated.

The bias mechanism 347 may be configured in a suitable manner such that a first end of the bias mechanism 347 may act on the actuator 306 and a second end of the bias mechanism 347 may act on the housing 302 and/or other component of the adapter 300. In some cases, the first end and/or the second end of the bias mechanism 347 may act on a support of or extending from the actuator 306 or the housing 302 (e.g., the support 349 extending from the housing 302). Although a spring may be shown as the bias mechanism 347 in FIG. 16, the bias mechanism 347 may include a pneumatic system, a hydraulic system, an electrical system, an electromechanical system, and/or other suitable biasing configuration.

Figure 17:
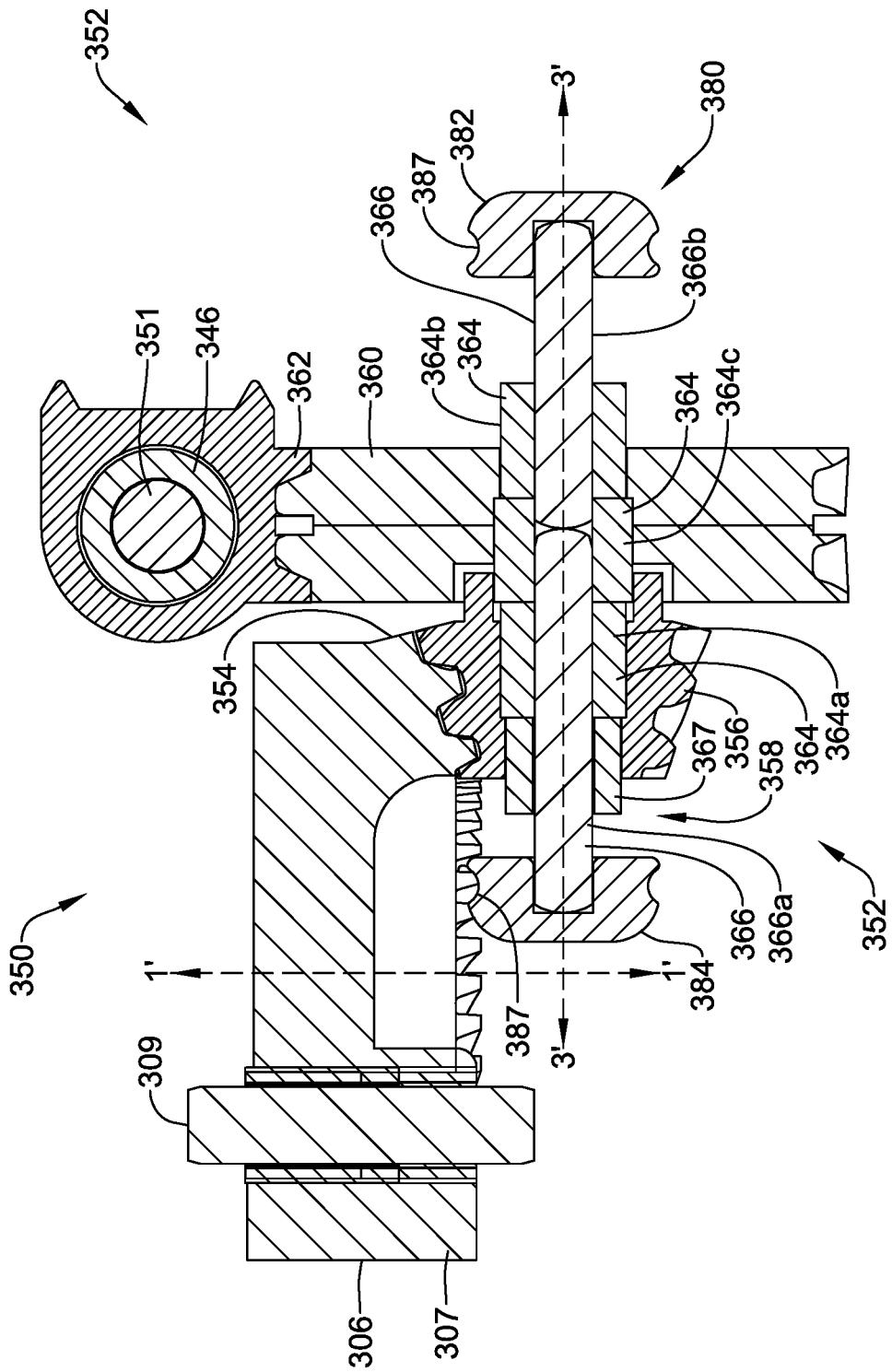
FIG. 17 is a cross-sectional view of a portion of an actuation system of the example adapter of FIG. 14, taken along line 17-17 in FIG. 16.

FIG. 17 depicts a cross-sectional view of a portion of the actuation system 350 of the adapter 300 with the housing 302 removed, taken along line 17-17 in FIG. 16. As mentioned, the actuation system 350 may include the actuator 306 (e.g., includes the arm 307), the adjustable portion 326 of the syringe holder 308 (not shown in FIG. 17), the linear guide track 346, the linear guide 351, the gear system 352, and/or one or more other components. Although the actuation system 350 is depicted and described as having the gear system 352, it is contemplated that the actuation system 350 may additionally or alternatively include one or more other suitable systems for causing movement of the adjustable portion 326 in response to movement of the actuator 306 including, but not limited to, a pneumatic system, a hydraulic system, a pulley system, and/or other suitable actuation system that may include different gears and/or actuation mechanisms than what is discussed herein or no gears at all.

Although the gear system 352 may differ from the gear system 152 of the adapter 100 in certain aspects, the gear system 352 may be similar (e.g., functionally and/or structurally similar) to the gear system 152 in some aspects. For example, the gear system 352 may be secured or fixed relative to housing 302, the gripping portion 304, the syringe holder 308, and/or one or more other components of the adapter 300. Further, the gear system 352 may be in communication with the actuator 306 and the adjustable portion 326 of the syringe holder 308 to adjust or facilitate adjusting the adjustable portion 326 relative to the fixed portion 324 of the syringe holder 308 in response to actuation of the actuator 306. In some cases, the gear system 352 or a portion of the gear system 352 may be adjustable relative to the housing 302, the gripping portion 304, the syringe holder 308, the actuator 306, and/or one or more other components of the adapter 300 to facilitate configuring adapters 300 for different hand sizes of users, different sizes of syringes, different applications with which the adapter 300 may be used, and/or to facilitate one or more other need.

The drive gear 354 of the drive system 352 may include teeth (e.g., helical teeth, spur teeth, etc.) configured to engage teeth (e.g., helical teeth, spur teeth, etc.) of the drive pinion 356. In some cases, the teeth of the drive gear 354 and the teeth of the drive pinion 356 may be angled or beveled to engage one another in response to rotation of the drive gear 354 and cause the drive pinion 356 to rotate about an axis 3'-3' that may be perpendicular to an axis 1'-1' about which the drive gear 354 may rotate. Alternatively, the drive pinion 356 may be configured to rotate about an axis that may be parallel to or at any other angle with respect to the axis 1'-1' or other axis about which the drive gear 354 may rotate. The drive pinion 356 may be connected to and/or may be in communication with the ratchet system 358 such that the ratchet system 358 or at least part of the ratchet system 358 rotates with the drive pinion 156, but this is not required.

The ratchet system 358 may be suitably configured to facilitate loading the actuator 306 without movement of the adjustable portion 326 and actuating the actuator 306 to cause movement of the adjustable portion 326. In one example configuration of the ratchet system 358, the ratchet system 358 may include one or more one-way bearings 364 (e.g., one-way needle bearings or other one-way bearings) and one or more pin rods 366. As shown in FIG. 17, the ratchet system 358 may include three one-way bearings 364 (e.g., a first one-way bearing 364a, a second one-way bearing 364b, and a third one-way bearing 364c) and two pin rods 366 (e.g., a first pin rod 366a and a second pin rod 366b), where the one-way bearings 364 are configured to rotate independently of the pin rods 366 in a first rotational direction and are configured to rotate with the pin rods 366 in a second rotational direction opposite of the first rotational direction. The pin rods 366 may form the first and second selectors 382, 384, may be combined with one or more other components to form the first and second selectors 382, 384, or may otherwise be in communication with the first and second selectors 382, 384.

In some cases, the ratchet system 358 may include one or more spacers. In the example shown in FIGS. 17, the ratchet system 358 may include a spacer 369 adjacent the first one-way bearing 364a. Additionally or alternatively, the ratchet system 358 may not include a spacer, may include one or more spacers in addition to or as an alternative to the spacer 369, and/or may include one or more other suitable components.

The one-way bearings 364 and the pin rods 366 may be configured in a suitable manner for operating the adapter 300. In one example configuration of the one-way bearings 364 and the pin rods 366, the first one-way bearing 364a may engage the drive pinion 356 and the second one-way bearing 364b and/or the third one-way bearing 364c may engage the driven pinion 360, where the first pin rod 366a may slide to engage only the first one-way bearing 364a when the selector 380 is in a disengaged position and may slide to engage one or both of the second one-way bearing 364b and the third one-way bearing 364c, along with the first one-way bearing 364a, when the selector 380 is in an engaged position. The second pin rod 366b may be configured to only engage the second one-way bearing 364b and/or the third one-way bearing 364c when the selector 380 is in the engaged and/or disengaged position and adjustably prevent the first pin rod 366a from engaging the second one-way bearing 364b and/or the third one-way bearing 364c when the selector 380 is in the disengaged position. The pin rods 366 and the one-way bearings 364 may have keyed configurations and/or other suitable configurations to facilitate rotation of the pin rods 366 with the one-way bearings 364.

In some cases, only one pin rod 366 may be utilized and one of the first pin rod 366a and the second pin rod 366b may be omitted. Alternatively, more than two pin rods 366 may be utilized.

In one example configuration, the first pin rod 366a may be omitted and the second pin rod 366b (e.g., where the second pin rod 366b may be the only pin rod if the first pin rod 366a is omitted) may be configured to engage the first one-way bearing 364a and one or more of the second one-way bearing 364b, the third one-way bearing 364c, and, if included, one or more other one-way bearing engaging the driven pinion 360 when the selector 380 is in the engaged position. Further, when the first pin rod 366a is omitted, the second pin rod 366b may be spaced or otherwise disengaged from the first one-way bearing 364a and/or other one-way bearings engaged with the actuator 306 and/or the drive pinion 356 when the selector 380 is in the disengaged position.

Returning to the example configuration depicted in the Figures, the one-way bearings 364 and the pin rods 366 may be configured such that when the actuator 306 is loaded (e.g., in response to a force from the bias mechanism 347 acting on the actuator 306 or other force acting thereon), the first one-way bearing 364a allows for rotation of the drive pinion 356 without rotation of the first pin rod 366a. When the actuator 306 is actuated, the first one-way bearing 364a is configured to cause the first pin rod 366a to rotate with the drive pinion 356. As such, when the selector 380 is in the engaged position with the selector 380 pushed to the right in FIG. 17 and the first pin rod 366a may engage the second one-way bearing 364b and/or the third one-way bearing 364c, along with the first one-way bearing 364a (e.g., when the first pin rod 366a is engaging the first one-way bearing 364a and the third one-way bearing 364c and the second pin rod 366b is engaging the second one-way bearing 364b, as depicted in the configuration of FIG. 17), actuation of the actuator 306 and resulting rotation of the first pin rod 366a may cause rotation of the second one-way bearing 364b and/or the third one-way bearing 364c, which in turn may cause rotation of the driven pinion 360 and adjustment of the rack 362 and the adjustable portion 326 of the syringe holder 308. When the selector 380 is in the disengaged position with the first selector element 382 pushed to the left in FIG. 17 such that the first pin rod 366a may only engage the first one-way bearing 364a and the second pin rod 366b may engage the second one-way bearing 364b and/or the third one-way bearing 364c (e.g., the second pin rod 366b may engage both of the second one-way bearing 364b and the third one-way bearing 364c when both are included, as in the configuration of FIG. 17), the driven pinion 360, the rack 362, and the adjustable portion 326 (not depicted in FIG. 17) may be configured to be moved independent of movement of the actuator 306, the drive gear 354, the drive pinion 356, the first one-way bearing 364a, and the first pin rod 366a. Moreover, when the selector 380 is in the disengaged position and/or when the actuator 306 is otherwise disengaged from the adjustable portion 326 of the syringe holder 308, the second pin rod 366b may be spaced from or otherwise disengaged from the first one-way bearing 364a and/or, when included, other one-way bearings or components configured to move with movement of the actuator 306 to allow for movement of the driven pinion 360, the rack 362, and the adjustable portion 326 independent from movement of the actuator 306.

The rack 362 of the gear system 352 may be connected to and/or in communication with (e.g., secured to or secured relative to) the adjustable portion 326 of the syringe holder 308 (not shown in FIG. 17). As such, the adjustable portion 326 of the syringe holder 308 may be longitudinally adjusted with respect to the fixed portion 324 of the syringe holder 308 in response to longitudinal adjustment of the rack 362. Further, as shown in FIG. 17, the rack 162 may be secured to the linear guide 351 which is configured to adjust along the linear guide track 346 and ensure the rack 362 and the adjustable portion 326 of the syringe holder 308 may be longitudinally adjusted in a linear and consistent manner. The linear guide track 346 of the adapter 300 may be an elongated tubular member having an inner lumen. The linear guide 351 may be an elongated dowel, rod, or other suitable linear guide. In some cases, as depicted in FIG. 17, the inner lumen of the linear guide track 346 may be configured to receive the linear guide 351 to facilitate linear longitudinal movement of the linear guide track 346 and the adjustable portion 326 of the syringe holder 308 (not shown in FIG. 17, but which may be fixed relative to the linear guide track 346 such that the adjustable portion 326 and the linear guide track 346 may move together).

In some cases, the actuation system 350 of the adapter 300 may include a power assist that assists a user in actuating the actuator 306. The power assist may facilitate reducing an amount of force applied to the actuator 306 that is required to drive the syringe plunger, while still providing feedback to a user. In some cases, the power assist may sense actuation of the actuator 306 and initiate an actuation assist to reduce the amount of force a user is required to apply to the actuator 306 to drive the plunger. The power assist may be a mechanical assist, an electromechanical assist, and/or other suitable type of power assist.

FIGS. 18-21 depict steps in a technique for loading and actuating an actuator to aspirate fluid into a syringe 400 received within the adapter 300. A similar technique may be utilized for dispensing fluid.

Figure 18:
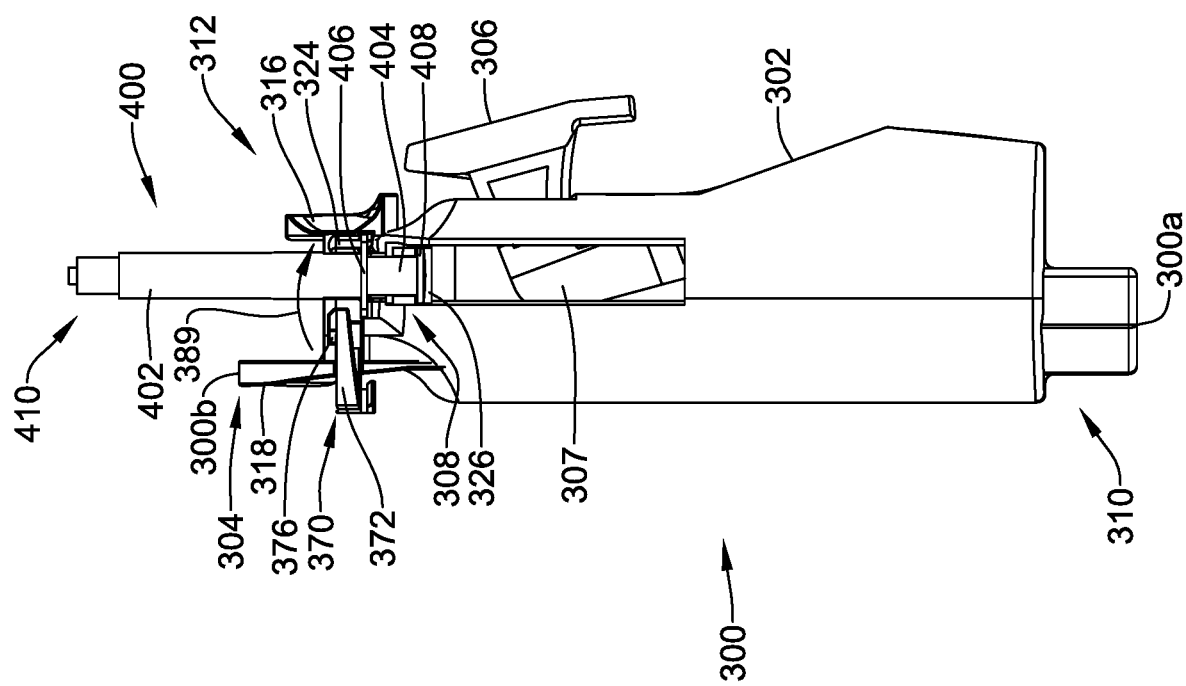
FIGS. 18-21 are side views of an example adapter depicting an aspirating technique.

FIG. 18 depicts the adapter 300 (e.g., the adapter 300 is depicted with a portion of the housing 302 removed) with a syringe 400 received in the fixed portion 324 and the adjustable portion 326 of the syringe holder 308, where a barrel 402 of the syringe 400 and/or a flange 406 of the barrel 402 may be received in the fixed portion 324 and a plunger 404 and/or a flange 408 of the plunger 404 may be received in the adjustable portion 326. Once the syringe 400 is within the adapter 300, the locking arm 372 of the locking mechanism 370 may be locked in place over the syringe 400 in a suitable manner, as discussed above, by rotating the locking arm in the direction of arrow 389. Alternatively or in addition, simply positioning the syringe 400 in the adapter 300 may result in locking the syringe 400 within the adapter 300 with the locking mechanism 370. The actuator 306 in FIG. 18 is in a loaded position (e.g., in response to a force of the bias mechanism 347 acting on the actuator 306) and the adjustable portion 326 of the syringe holder 308 may be maintaining the plunger 404 in a fully inserted position within the barrel 402.

Figure 19:
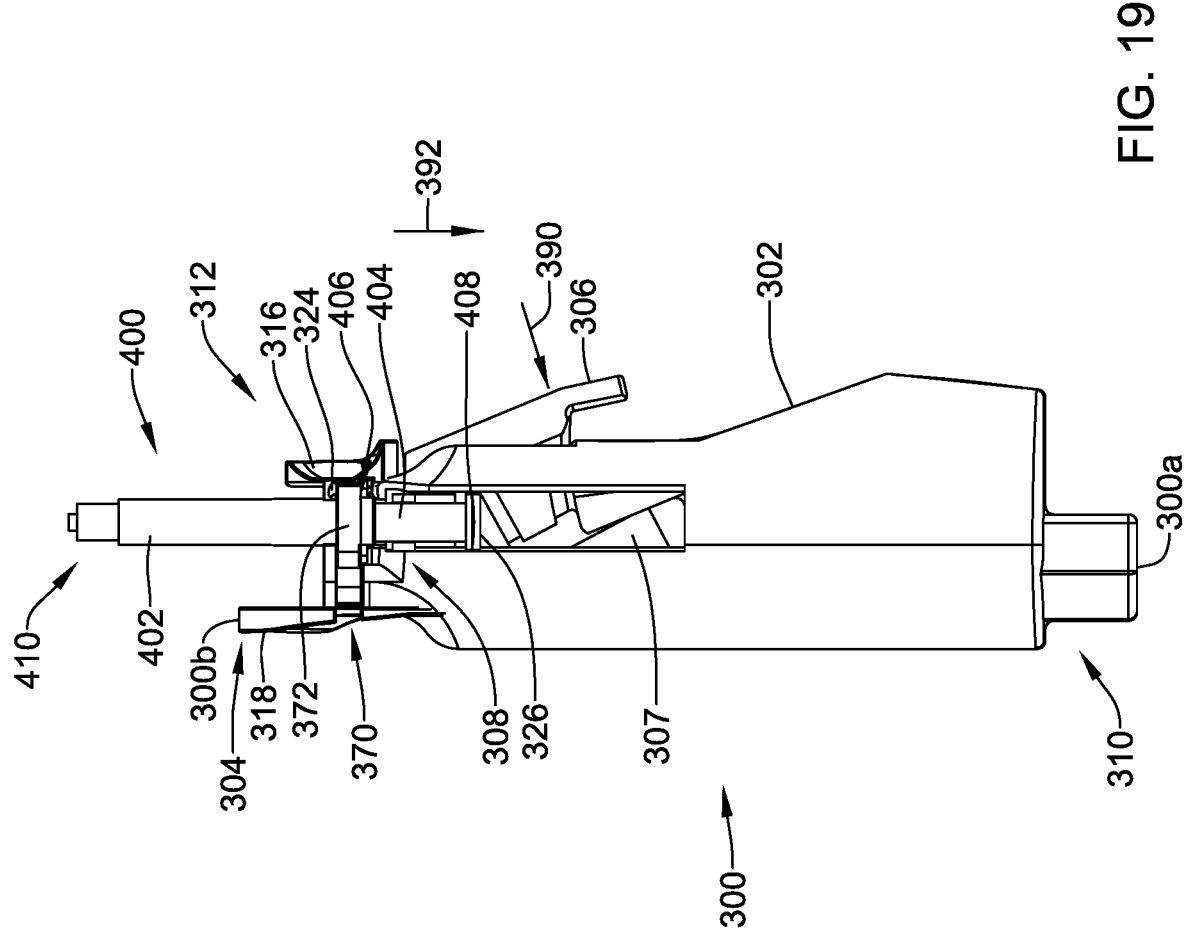

FIG. 19 depicts the syringe 400 within the adapter 300 with the locking mechanism 370 in a locked position to secure the syringe 400 in the adapter 300. Additionally, as can be seen in FIG. 19, the actuator 306 has been actuated with a force in the direction of arrow 390 or other lateral direction toward the syringe 400 acting against a force from the bias mechanism 347. In response to actuation of the actuator 306, the adjustable portion 326 of the syringe holder 308 may be adjusted in a direction of arrow 392 to cause the plunger 404 to withdraw from the barrel 402 of the syringe 400 and aspirate fluid into the barrel 402 of the syringe 400. In one example of actuating the actuator 306, a palmar flexion movement of one or more digits and/or other portion of a user's hand may be utilized to adjust the actuator 306 from a loaded position to an actuated position and adjust a position of the adjustable portion 326 of the syringe holder 308 relative to the fixed portion 324 of the syringe holder 308. Such a palmar flexion movement of one or more digits or other portions of a user's hand may be performed while two or more digits and/or a palm of the user's hand are engaged with the adapter 300 (e.g., the gripping portion 304 of the adapter 300). In some cases, a movement of a user's hand other than a palmar flexion movement may be utilized to actuate the actuator 306. Further, in some cases, the actuator 306 may be actuated by movement of a user's thumb (e.g., a user's first digit).

Figure 20:
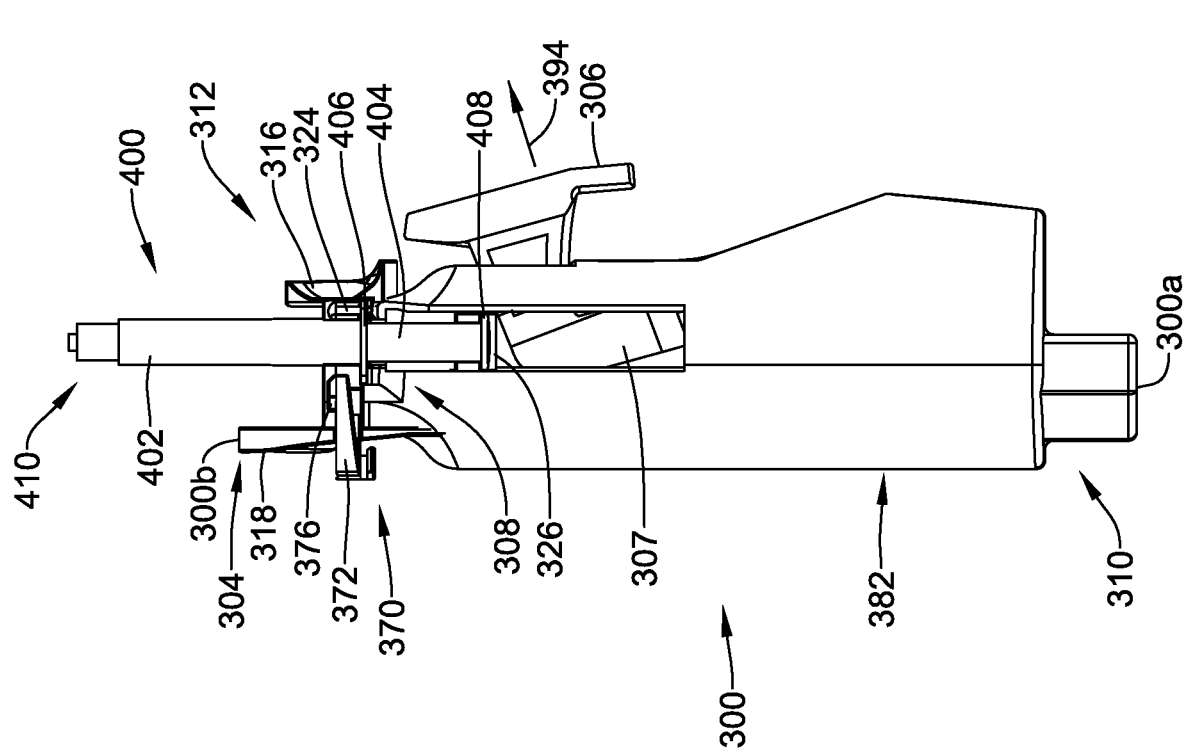

FIG. 20 depicts the syringe 400 within the adapter 300 with the actuator 306 in a loaded position (e.g., in response to a force applied thereto by the bias mechanism 347 in a direction of arrow 396) and the adjustable portion 326 of the syringe holder 308 in a completely withdrawn position. The adjustable portion 326 may be in the completely withdrawn position in response to a single actuation of the actuator 306 or two or more actuations of the actuator 306 depending on a configuration of the gear system 352, as desired. Further, as the adjustable portion 326 is in a completely withdrawn position with the syringe 400 ready for removal, the locking arm 372 of the locking mechanism 370 may be unlocked from the housing 302 of the adapter 300 to facilitate removal of the syringe 400 from the adapter 300. In some cases, the locking arm 372 may be unlocked from the housing 302 by applying a force to the locking arm 372 (e.g., applying a force to a tab or other portion of the locking arm 372) to disengage the locking arm 372 from the housing 302. Once the locking arm 372 is unlocked from the housing 302, the syringe 400 may be removed from the adapter 300.

Figure 21:
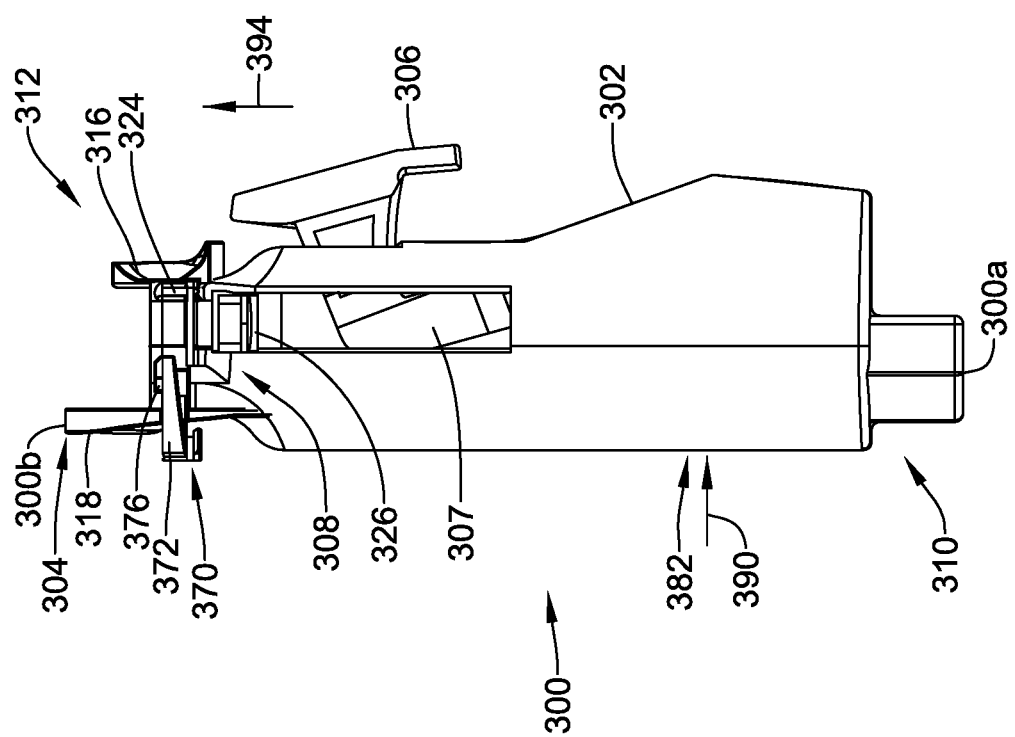

FIG. 21 depicts the adapter 300 with the locking mechanism 370 in an unlocked position and the syringe 400 removed from the adapter 300. Although not depicted in FIG. 21 due to the housing 302 covering a portion of the actuation system 350, the first selector element 382 may be pushed in the direction of the arrow 386 in FIG. 15 such that the one-way bearing(s) engaging the driven pinion 360 (e.g., the second one-way bearing 364b and the third one-way bearing 364c depicted in FIG. 17) are disengaged from the first pin rod 366a in communication with the one-way bearing(s) engaging the drive pinion 356 (e.g., the first one-way bearing 364a) to allow the adjustable portion 326 of the syringe holder 308 to be moved independently of the actuator 306. When the adjustable portion 326 is able to move independently of the actuator 306, the adjustable portion 326 may be manually moved, or moved in one or more other suitable manners, in a direction of arrow 394 to a syringe loading position as depicted in FIG. 21. In some cases, the adapter 300 may have a ball detent configured to provide tactile and/or audible feedback when the adjustable portion 326 is adjusted to a desired syringe loading position and/or one or more other desired locations.

As mentioned above, FIGS. 22-25 depict various features of syringe attachment devices or adapters in the context of the illustrative syringe attachment device or adapter 500. The adapter 500 may include features that are similar to features of the adapter 100 and/or features that are similar to features of the adapter 300 described above and/or additional or alternative features to the features of the adapter 100 and/or the adapter 300. Although such details of features may not be particularly discussed with respect to the adapter 500, the details of the adapter 100 and/or the adapter 300 may be additionally or alternatively incorporated into the adapter 500 and the details of features discussed with respect to the adapter 500 may be additionally or alternatively incorporated into the adapter 100 and/or the adapter 300, unless clearly indicated otherwise.

Figure 22:
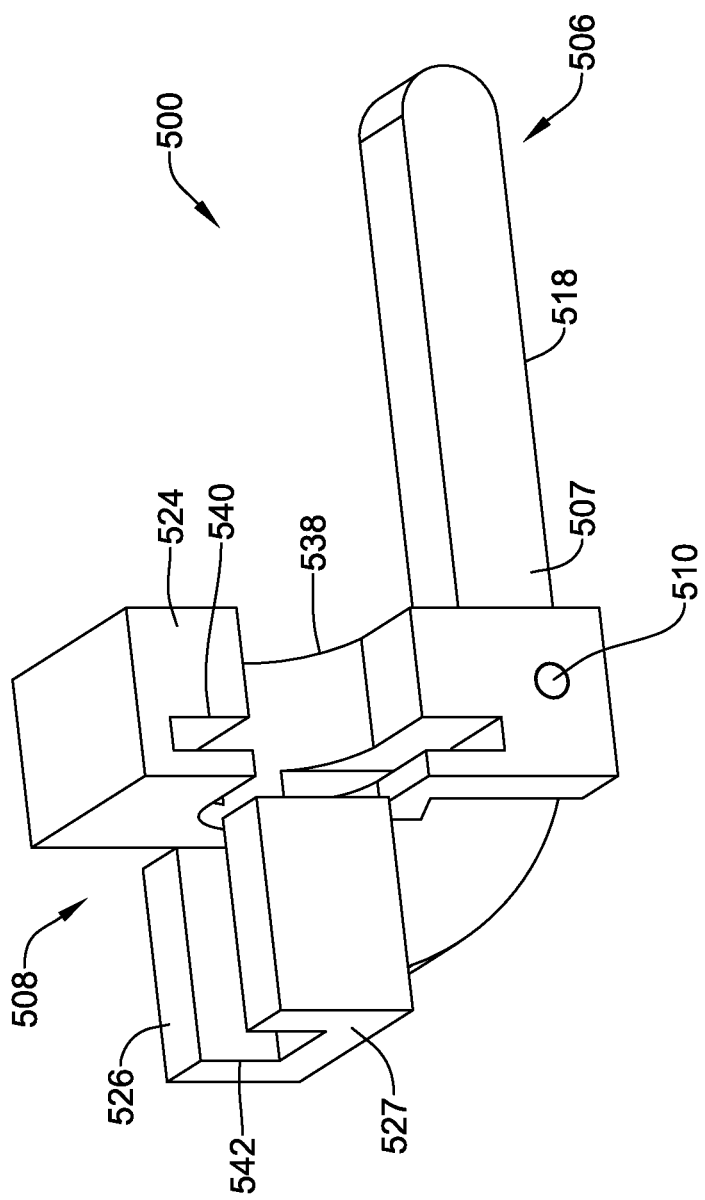
FIG. 22 is a perspective view of an example adapter for use with a syringe, as seen from a first side of the example adapter.
Figure 23:
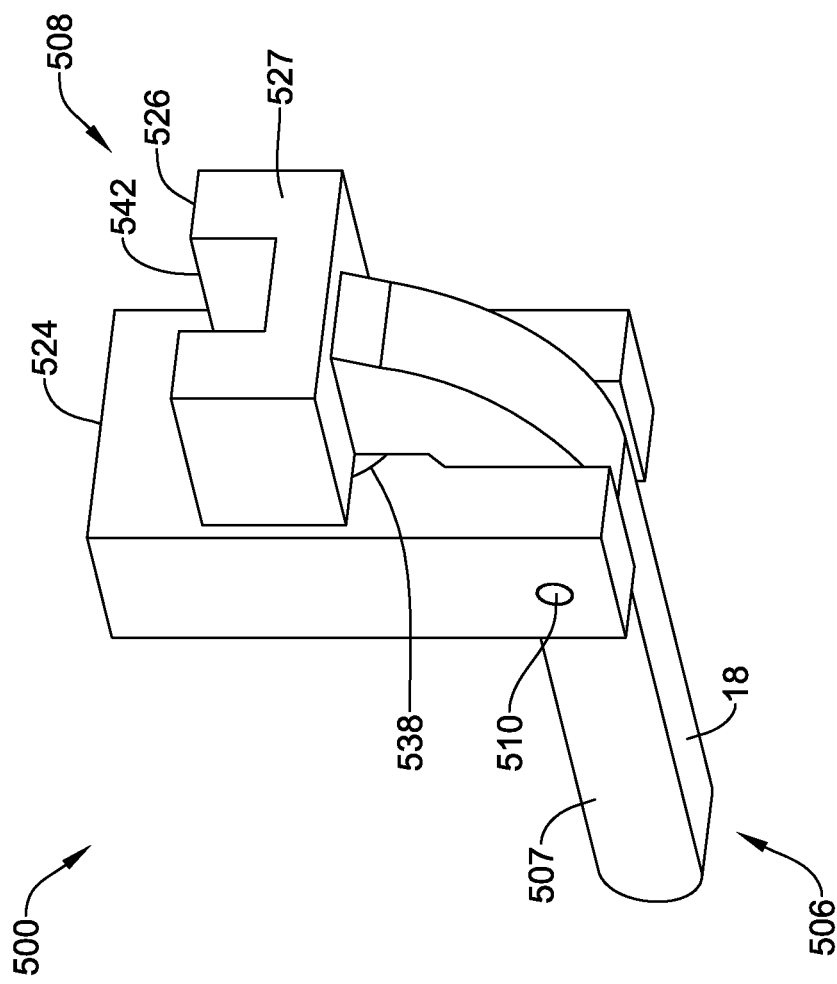
FIG. 23 is a perspective view of the example adapter of FIG. 22, as seen from a second side of the example adapter.

FIGS. 22 and 23 are perspective views of the illustrative adapter 500 that is configured to be used with a syringe (e.g., the syringe 2 or other syringe), taken from a first side of the adapter 500 and a second side of the adapter 500, respectively. The adapter 500 may include an actuator 506 and a syringe holder 508, among one or more other suitable components.

In some cases, the adapter 500 may be configured to be actuated in response to one or more components pivoting about a pivot element 510. The pivot element 10 may be a pivot pin or other suitable element facilitating pivot movements of one or more components of the adapter 500. Although the adapter 500 depicted in FIGS. 22-25 may be configured such that the actuator 506 is configured to rotate (e.g., pivot) about the pivot element 510, the actuator 506 and/or other component of the adapter 500 may be configured to rotate about one or more additional or alternative pivot elements, as desired.

The actuator 506 may be or may include a grip portion 518 configured to receive one or more digits and/or a palm of a user's hand such that the one or more digits or palm of a user's hand may apply a force to the actuator 506 via a palmar flexion movement or other movement of the user. In operation, the actuator 506 may be manually (as depicted in FIGS. 22-25) or automatically (e.g., in response to a bias mechanism (not depicted)) loaded in a first direction (e.g., a laterally outward direction) relative to the syringe holder 508 or a syringe received in the syringe holder 508 and actuated in response to a force from the user acting on the grip portion 518 in a second direction (e.g., a laterally inward direction) to drive a portion of the syringe holder 508. Alternatively or in addition, one or more portions of the grip portion 518 may be engaged by one or more digits or other portions of a hand of a user in one or more suitable manners other than during laterally inward and/or outward motions relative to the syringe holder 508 and/or a syringe received therein to drive a portion of the syringe holder 508. Movement of actuator 506 will be described in greater detail below.

The grip portion 518 of the actuator 506 may be configured to receive one or more digits of a user. As shown in FIGS. 22 and 23, the grip portion 518 of the actuator 506 may be elongated and configured to receive a palm and/or a plurality of digits of a user. Alternatively, the actuator 506 may be configured to receive a single digit or only a palm of a user. Although the adapter 500 may be configured to easily allow a user to aspirate fluid into a syringe and/or dispense fluid from the syringe by engaging the actuator 506 with a single digit, having an actuator 506 that may accept a plurality of digits and/or a palm may further reduce stress on a user's hand, wrist, and/or forearm areas in response to actuating the actuator 506.

In some cases, the grip portion 518 of the actuator 506 may be angled to facilitate a user actuating the actuator 506. In one example, the grip portion 518 may be angled about fifteen (15) degrees relative to a longitudinal axis of the adapter 500. Such an angle may facilitate actuation of the actuator 506 in a biomechanically efficient manner. Other angles of the grip portion 518 are contemplated. For example, the angle of the grip portion 518 may be different if a user's first digit is intended to actuate the actuator 506 than if a user's third digit is intended to actuate the actuator 506, but this is just an example and is not required.

Similar to the grip portions 114, 116, 118, 314, 316, 318, the grip portion 518 may be configured in a suitable manner. In some cases, the grip portion 518 may be a side of the actuator 506. Alternatively or in addition, the grip portion 518 may be or may include one or more surfaces (e.g., surfaces with grip features such as indents, protrusions, bumps, recesses, and/or other suitable grip features), one or more flanges, one or more supports, and/or other suitable structure configured to facilitate maintaining a grip when engaging the gripping the actuator 506.

The actuator 506 may include an arm 507 extending to and/or beyond the pivot element 510. The arm 507 may be similar to the arm 307, but this is not required. In some cases, the arm may extend to the syringe holder 508. Further, the arm 507, and thus the actuator 506, may be configured to pivot about an axis extending through the pivot element 510 such that movement of the actuator 506 may cause movement of at least a portion of the syringe holder 508.

The syringe holder 508 may include, among other components, a fixed portion 524 (e.g., a fixed first portion) and an adjustable portion 526 (e.g., an adjustable second portion). The fixed portion 524 of the syringe holder 508 may be configured to receive a barrel (e.g., the barrel 4 or other barrel of a syringe), a barrel flange (e.g., the barrel flange 14 or other barrel flange of a syringe), and/or other or more other portion of a barrel of a syringe. The adjustable portion 526 of the syringe holder 508 may be configured to receive a plunger flange (e.g., the plunger flange 16 or other plunger flange of a syringe), a plunger stem, and/or other portion of a plunger of a syringe. The components of the syringe holder 508 may be adjustable or otherwise configured to receive different sizes of syringes. In some cases, the fixed portion 524 and the adjustable portion 526 may be formed from one or more components and configured in a manner similar to how the fixed portions 124, 324 and the adjustable portions 126, 326 of the adapters 100, 300 are configured, but this is not required.

The adjustable portion 526 of the syringe holder 508 may be part of, connected to, and/or otherwise in communication with the arm 507 and/or other portion of the actuator 506 of the adapter 500. As shown in FIGS. 22 and 23, the arm 507 of the actuator 506 is formed with and rigidly fixed with respect to the adjustable portion 526 of the syringe holder 508.

In some cases, the adjustable portion 526 may be axially and/or longitudinally adjustable relative to the fixed portion 524 of the syringe holder 508 in response to actuation of the actuator 506. As the adjustable portion 526 may be configured to receive and/or engage a plunger of a syringe, adjusting the adjustable portion 526 of the syringe holder 508 may result in aspirating fluid into the syringe (e.g., as in the configuration of the adapter 500 depicted in FIGS. 22-25) and/or dispensing fluid from the syringe.

The fixed portion 524 and/or the adjustable portion 526 may be configured to secure the syringe in the syringe holder 508 via a friction fit, a snap fit, and/or through other securing mechanisms. In some cases, the fixed portion 524 and/or the adjustable portion 526 may include adjustable components that are adjustable to facilitate different sizes of syringes. In one example, one or more of the fixed portion 524 and the adjustable portion 526 may include one or more inserts or sub-adapters for accommodating and/or securing different sizes of plunger flanges, barrel flanges, or other components of a syringe within the syringe holder 508. Such inserts may be releasably connected to and/or positioned within the syringe holder 508.

The fixed portion 524 and the adjustable portion 526 of the syringe holder 508 may include one or more slots for receiving a flange or other portion of a syringe. For example, as shown in FIG. 22, the fixed portion 524 may include a barrel slot 538 for receiving a barrel of a syringe and a barrel flange slot 540 for receiving a barrel flange of a syringe and the adjustable portion 526 may include a plunger receiving slot 542 for receiving a plunger stem of the syringe. The plunger receiving slot 542 may be configured to receive a plunger or plunger stem such that a flange of the plunger stem may engage an end 527 of the adjustable portion 526 to apply a force to a flange of the plunger and facilitate withdrawing the plunger from the barrel of the syringe in response to actuation of the actuator 506. Additionally or alternatively, the adjustable portion 526 may include a syringe flange slot similar to or different than the barrel flange slot 540 discussed above.

Although the plunger receiving slot 542 and the barrel slot 538 (and the barrel flange slot 540) are depicted in FIG. 22 as having openings that open in different direction, the plunger receiving slot 542 and the barrel slot 538 may have openings that open in a same direction or openings that open in different directions other than what is depicted in FIG. 22 and that facilitate receiving a syringe within the adapter 500.

In some cases, the barrel slot 538, the barrel flange slot 540, and/or the plunger receiving slot 542 may be configured to create a friction fit or other engaging fit with a barrel, a barrel flange, or plunger, respectively, received therein. Additionally or alternatively, as discussed above, one or more of the barrel slot 538, the barrel flange slot 540, and the plunger receiving slot 542 may be configured to receive an insert (e.g., a sub-adapter), where the insert may have a slot configured to receive a barrel, a stem, and/or a flange of a syringe that is too small or too large to fit in one of the barrel slot 538, the barrel flange slot 540, or the plunger receiving slot 542. Use of an insert or other similar feature may facilitate using the adapter 500 with various sizes of syringes. Other mechanisms for attaching a syringe to the adapter 500 are contemplated including, but not limited to, a releasable locking mechanism.

Although not depicted in FIGS. 22-25, the syringe holder 508 or other suitable portion of the adapter 500 may include a locking mechanism configured to facilitate securing a received syringe within the adapter 500. In some cases, the locking mechanism may be adjustable (e.g., automatically and/or manually adjustable) to releasably secure a received syringe within the adapter 500.

In some cases, the adapter 500 may include a power assist that assists a user in actuating the actuator 506. The power assist may facilitate reducing an amount of force applied to the actuator 506 that is required to drive the syringe plunger, while still providing feedback to a user. In some cases, the power assist may sense actuation of the actuator 506 and initiate an actuation assist to reduce the amount of force a user is required to apply to the actuator 506 to drive the plunger. The power assist may be a mechanical assist, an electromechanical assist, and/or other suitable type of power assist.

Figure 24:
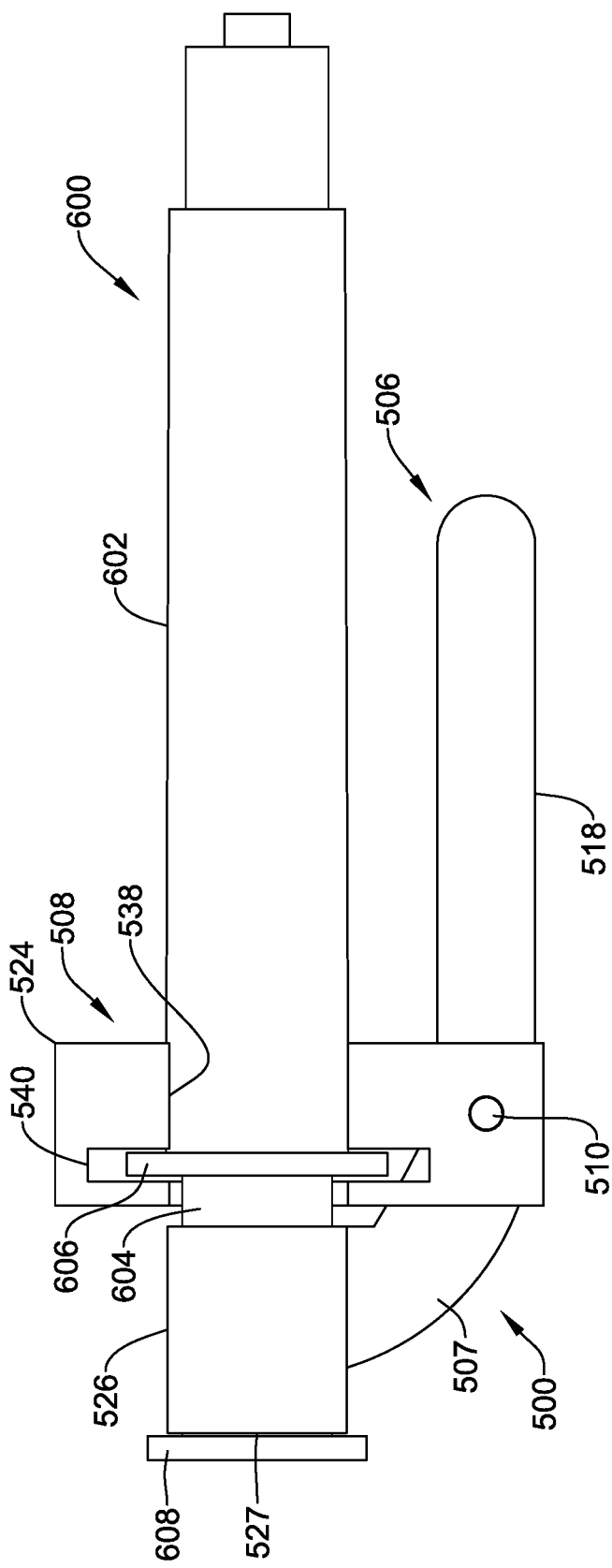
FIGS. 24 and 25 are side view of an example adapter with a received syringe depicting an aspirating technique.
Figure 25:
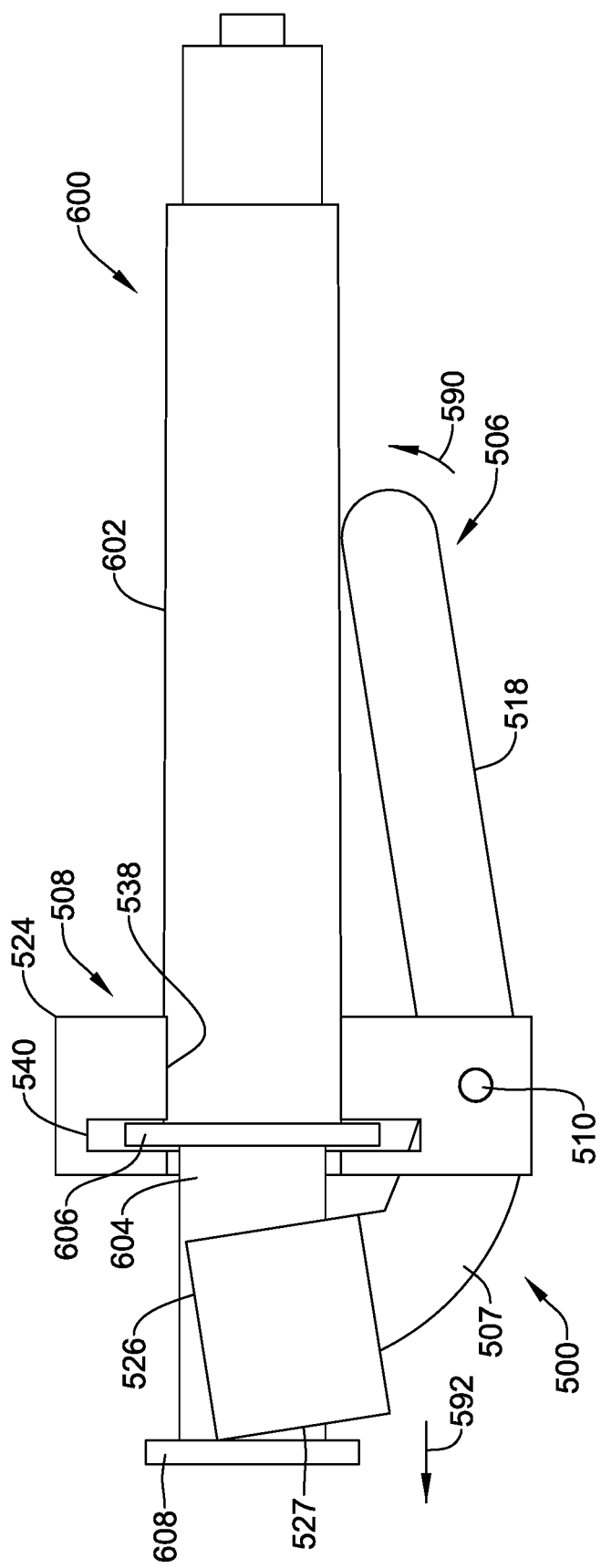

FIGS. 24 and 25 depict steps in a technique for actuating an actuator to aspirate fluid into a syringe 600 and/or create a vacuum within the syringe 600. FIG. 25 depicts the adapter 500 with the syringe 600 received in the fixed portion 524 and the adjustable portion 526 of the syringe holder 508, where a barrel 602 of the syringe 600 and/or a flange 606 of the barrel 602 may be received in the fixed portion 524 (e.g., the barrel 602 may be received in the barrel slot 538 and the barrel flange 606 may be received in barrel flange slot 540) and a plunger 604 may be received in the adjustable portion 526. The syringe 600 may be received within or otherwise positioned in the adapter 500 such that a flange 608 of the plunger 604 may abut or may at least be adjacent to the end 527 of the adjustable portion 526 such that when the actuator 506 is actuated, the adjustable portion 526 engages the flange 608 to withdraw the plunger 604 a desired distance out of the barrel 602 to aspirate fluid into the barrel 602 and/or create a vacuum within the barrel 602.

FIG. 25 depicts the syringe 600 within the adapter 500 with the actuator 506 in an actuated positions. The actuator 506 may be actuated with a force in a direction of arrow 590 or other lateral direction toward the syringe 600. In response to actuation of the actuator 506, the adjustable portion 526 of the syringe holder 508 may be adjusted in a direction of arrow 592 to cause the plunger 604 to withdraw from the barrel 602 of the syringe 400 and aspirate fluid into the barrel 602 and/or create a vacuum within the barrel 602. In one example, a full actuation of the actuator 506 may result in adjustment of the flange 608 of the plunger 604 moving a distance in a range of about three (3) millimeters to about ten (10) millimeters, or other suitable distance. In some cases, a configuration of the actuator 506 relative to the syringe holder 508 may facilitate determining a maximum total distance of plunger withdrawal in response to a single actuation of the actuator 506.

In one example of actuating the actuator 506, a palmar flexion movement of one or more digits and/or other portion of a user's hand may be utilized to adjust the actuator 506 from a loaded position to an actuated position and adjust a position of the adjustable portion 526 of the syringe holder 508 relative to the fixed portion 524. Such a palmar flexion movement of one or more digits or other portions of a user's hand (e.g., one or more of the third digit, the fourth digit, and the fifth digit of a user's hand) may be performed while two or more digits of the user's hand (e.g., a first digit and a second digit of a user's hand) are engaged with and/or maintaining a position of the syringe 600. In some cases, a movement of a user's hand other than a palmar flexion movement may be utilized to actuate the actuator 506.

Further, in some cases, the actuator 506 may be actuated by movement of a user's thumb (e.g., a user's first digit).

The adapter 500 may be utilized in suitable medical procedures. Example medical procedures may include central line placement procedures, thoracentesis procedures, other procedures in which a user is to slightly withdraw the syringe in order to create a vacuum within the syringe 600, and/or other suitable procedures. When using the adapter 500 in a central line placement procedure and/or a thoracentesis procedure, a medical practitioner may close their hand around the adapter 500 (e.g., with a palmar flexion movement or other movement) to create a vacuum within the barrel 602 of the syringe 600. Such a movement to create a vacuum within the syringe 600 is biomechanically superior to typical movements needed to withdraw a plunger from a barrel during central line placement or thoracentesis.

The components of the adapter 100, the adapter 300, the adapter 500, and/or other suitable adapters including one or more of the housing 102, 302, the gripping portion 104, 304, the actuator 106, 306, 506, the syringe holder 108, 308, 508, and the gear system 152, 352 may be formed from any material. For example, the housing 102, 302, the gripping portion 104, 304, the actuator 106, 306, 506, the syringe holder 108, 308, 508, and/or the gear system 152, 352 may be formed from a mechanically robust material that may withstand repeated use without failure, including but not limited to one or more of one or more metals and one or more polymers. In one example, one or more of the housing 102, 302, the gripping portion 104, 304, the actuator 106, 306, 506, the syringe holder 108, 308, 508, the gear system 152, 352, components thereof, and/or other components of the adapters 100, 300, 500 may be configured from polypropylene, polycarbonate, polyamide, photopolymer, and/or stainless steel, but this is not required.

The components of the adapters 100, 300, 500 may be formed in any suitable manner. In some cases, one or more components and/or parts of the adapter 100, 300, 500 may be formed from three-dimensional (3D) printing, molding, grinding, lathing, surfacing, and/or one or more other forming and/or configuring techniques.

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A handheld syringe adapter comprising:
   a body configured to receive a syringe, wherein the body comprises:
      a fixed first portion;
      an adjustable second portion that is adjustable with respect to the fixed first portion;
      a first end portion adjacent a first end of the body; and
      a second end portion adjacent a second end of the body opposite the first end;
   an actuator laterally adjustable about a first axis;
   a gear system having one or more gear components rotatable about a second axis, the second axis is non-parallel with the first axis, wherein actuation of the actuator about the first axis causes rotation of the one or more gear components about the second axis and adjusts a position of the adjustable second portion; and
   a selector configured to:
      engage the actuator with the adjustable second portion such that actuation of the actuator about the first axis adjusts the position of the adjustable second portion; and
      disengage the actuator with the adjustable second portion such that the adjustable second portion is freely adjustable.

2. A one-handed syringe adapter comprising:
   a syringe holder having a fixed portion and an adjustable portion adjustably positioned relative to the fixed portion, where the fixed portion is configured to receive a barrel of a syringe and the adjustable portion is configured to receive a plunger of the syringe;
   an actuator selectively actuated with a palmar flexion movement of one or more digits of a user's hand to adjust a position of the adjustable portion of the syringe holder relative to the fixed portion of the syringe holder while two or more digits of the user's hand engage the syringe adapter; and
   a gear system secured relative to the syringe holder, the gear system is in communication with the actuator and the adjustable portion of the syringe holder to adjust the adjustable portion relative to the fixed portion in response to actuation of the actuator; and
   wherein the gear system comprises:
      a rack with teeth, the rack is secured relative to the adjustable portion of the syringe holder and the adjustable portion of the syringe holder is configured to adjust with respect to the fixed portion of the syringe holder in response to movement of the rack;
      a driven pinion configured to engage the teeth of the rack and move the rack in response to movement of the driven pinion;
      a ratchet system configured to drive the driven pinion;
      a drive pinion in communication with the ratchet system;
      a drive gear in communication with the drive pinion; and
      wherein the drive gear rotates in response to actuation of the actuator to drive the driven pinion and adjust the adjustable portion of the syringe holder.

3. The adapter of claim 2, wherein the actuator is configured to be in a loaded position in response to movement of the actuator in a first direction and the actuator is configured to be in an actuated position in response to movement of the actuator in a second direction.

4. The adapter of claim 3, wherein the movement of the actuator in the first direction causes an audible indication indicative of a distance the adjustable portion of the syringe will move in response to the movement of the actuator in the second direction.

5. The adapter of claim 3, wherein the movement of the actuator in the first direction causes a tactile indication indicative of a distance the adjustable portion of the syringe will move in response to the movement of the actuator in the second direction.

6. The adapter of claim 2, wherein the actuator is configured to rotate about an axis.

7. The adapter of claim 2, further comprising:
   a first grip portion;
   a second grip portion and
   wherein the first grip portion and the second grip portion are:
      fixed relative to the fixed portion of the syringe holder; and
      configured to receive the two or more digits of the user's hand.

8. The adapter of claim 7, wherein the actuator is laterally offset, longitudinally offset, or both laterally offset and longitudinally offset from the first grip portion and the second grip portion.

9. The adapter of claim 2, further comprising:
a housing covering at least part of the gear system; and
a locking element configured to releasably engage the housing to secure the syringe at least partially within the housing.

10. The adapter of claim 2, wherein the ratchet system is reversible.

11. The adapter of claim 2, further comprising:
a selector configured to selectively engage and disengage the actuator with the driven pinion.

12. A handheld syringe adapter comprising:
a body configured to receive a syringe, wherein the body comprises:
   a fixed first portion;
   an adjustable second portion that is adjustable along a first axis with respect to the fixed first portion;
   a first end portion adjacent a first end of the body; and
   a second end portion adjacent a second end of the body opposite the first end;
an actuator laterally adjustable about a second axis, the second axis is non-parallel with the first axis;
a gear system having one or more gear components rotatable about a third axis, the third axis is non-parallel with the first axis and the second axis; and
wherein actuation of the actuator about the second axis causes rotation of the one or more gear components about the third axis and adjusts a position of the adjustable second portion along the first axis.

13. The adapter of claim 12, further comprising:
a first grip portion adjacent the second end portion of the body;
a second grip portion adjacent the second end portion of the body; and
wherein the second grip portion is spaced from the first grip portion a distance that is configured to be greater than a diameter of a barrel of the syringe.

14. The adapter of claim 12, further comprising:
a selector configured to:
   engage the actuator with the adjustable second portion such that actuation of the actuator about the second axis adjusts the position of the adjustable second portion; and
   disengage the actuator with the adjustable second portion such that the adjustable second portion is freely adjustable.

* * * * *